United States Patent
Nguyen

(10) Patent No.: US 9,738,620 B2
(45) Date of Patent: Aug. 22, 2017

(54) TRIENTINE PRODRUGS, PHARMACEUTICAL COMPOSITIONS THEREOF, AND METHODS OF USE

(71) Applicant: Mark Quang Nguyen, San Jose, CA (US)

(72) Inventor: Mark Quang Nguyen, San Jose, CA (US)

(73) Assignee: Mark Quang Nguyen, San Jose, CA (US)

( * ) Notice: Subject to any disclaimer, the term of this patent is extended or adjusted under 35 U.S.C. 154(b) by 13 days.

(21) Appl. No.: 14/935,407

(22) Filed: Nov. 7, 2015

(65) Prior Publication Data

US 2017/0129868 A1    May 11, 2017

(51) Int. Cl.
| | | |
|---|---|---|
| *C07D 211/72* | (2006.01) | |
| *C07D 211/84* | (2006.01) | |
| *C07D 213/69* | (2006.01) | |
| *C07D 213/70* | (2006.01) | |
| *A61K 31/44* | (2006.01) | |
| *C07D 317/40* | (2006.01) | |
| *C07C 271/22* | (2006.01) | |

(52) U.S. Cl.
CPC .......... *C07D 317/40* (2013.01); *C07C 271/22* (2013.01); *C07C 2101/14* (2013.01)

(58) Field of Classification Search
None
See application file for complete search history.

(56) References Cited

PUBLICATIONS

Lu, J. Triethylenetetramine Pharmacology and Its Clinical Applications. Molecular Cancer Therapeutics. 2010, vol. 9, p. 2459.*
Gilmer, JF. et al. Prodrugs for Amines. Molecules. 2008, vol. 13, p. 521.*

* cited by examiner

*Primary Examiner* — Noble Jarrell
*Assistant Examiner* — Ben S Michelson

(57) ABSTRACT

Trientine prodrugs, pharmaceutical compositions comprising the trientine prodrugs, and methods of using trientine prodrugs and pharmaceutical compositions thereof for treating Wilson's disease.

20 Claims, No Drawings

TRIENTINE PRODRUGS, PHARMACEUTICAL COMPOSITIONS THEREOF, AND METHODS OF USE

FIELD

Disclosed herein are trientine prodrugs, pharmaceutical compositions comprising trientine prodrugs, and methods of using trientine prodrugs and pharmaceutical compositions thereof for treating Wilson's disease.

BACKGROUND

Trientine is approved in United States to treat patient with Wilson's disease who are intolerant of D-penicillamine or tiopronin.

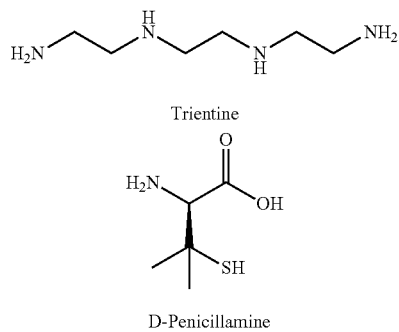

Trientine

D-Penicillamine

However, trientine exhibits poor oral absorption characteristics. Trientine has an oral bioavailability of 8-30% (Lu., Molecular Cancer Therapeutics. 2010, 9 (9), 2458-67) and requires up to four-times-a-day dosing.

SUMMARY

Trientine prodrugs having high gastrointestinal permeability and/or absorption and minimal degradation/cleavage in the gut lumen or enterocyte cytoplasm are desirable. Such trientine prodrugs, which provide higher oral bioavailability and plasma levels of the parent compound, trientine, may: enhance the efficacy/responder rate compared to present trientine; facilitate the use of lower doses, reduce dosing frequency, and standardize dosing regimens; reduce food effects; reduce gastrointestinal side effects/toxicity; and reduce interpatient treatment variability.

In a first aspect, compounds of Formula (I) are provided:

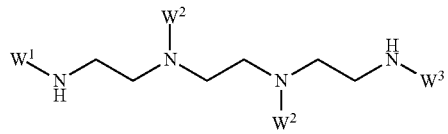

(I)

or a pharmaceutically acceptable salt thereof, wherein:

$W^1$ is chosen from substituents of Formula (I-a) and Formula (I-b); and each $W^2$ and $W^3$ is independently chosen from hydrogen and substituents of Formula (I-a) and Formula (I-b):

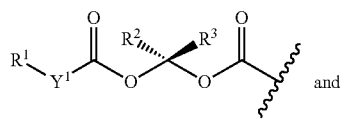

(I-a)

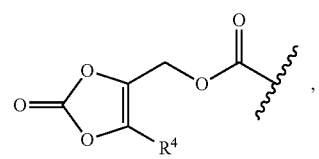

(I-b)

wherein
$R^1$, $R^2$, $R^3$, and $R^4$ are independently chosen from hydrogen, $C_{1-6}$ alkyl, $C_{1-6}$ heteroalkyl, $C_{3-12}$ cycloalkyl, $C_{3-12}$ heterocycloalkyl, $C_{5-10}$ aryl, and $C_{5-10}$ heteroaryl; and
$Y^1$ is chosen from a bond and —O—.

In a second aspect, pharmaceutical compositions are provided comprising a compound of Formula (I) and at least one pharmaceutically acceptable vehicle.

In a third aspect, methods of treating a disease in a patient are provided comprising administering to a patient in need of such treatment a pharmaceutical composition comprising a therapeutically effective amount of a compound of Formula (I). In certain embodiments, the disease is chosen from a Wilson's disease.

DETAILED DESCRIPTION

Definitions

A dash ("-") that is not between two letters or symbols is used to indicate a point of attachment for a moiety or substituent. For example, —CONH₂ is bonded through the carbon atom.

"Alkyl" refers to a saturated or unsaturated, branched, or straight-chain, monovalent hydrocarbon radical derived by the removal of one hydrogen atom from a single carbon atom of a parent alkane, alkene, or alkyne. Examples of alkyl groups include, but are not limited to, methyl; ethyls such as ethanyl, ethenyl, and ethynyl; propyls such as propan-1-yl, propan-2-yl, prop-1-en-1-yl, prop-1-en-2-yl, prop-2-en-1-yl(allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds, and groups having combinations of single, double, and triple carbon-carbon bonds. Where a specific level of saturation is intended, the terms alkanyl, alkenyl, and alkynyl are used. In certain embodiments, an alkyl group can have from 1 to 20 carbon atoms ($C_{1-20}$) in certain embodiments, from 1 to 10 carbon atoms ($C_{1-10}$), in certain embodiments from 1 to 8 carbon atoms ($C_{1-8}$), in certain embodiments from 1 to 6 carbon atoms ($C_{1-6}$), in certain embodiments from 1 to 4 carbon atoms ($C_{1-4}$), and in certain embodiments, from 1 to 3 carbon atoms ($C_{1-3}$).

"Aryl" refers to a monovalent aromatic hydrocarbon radical derived by the removal of one hydrogen atom from a single carbon atom of a parent aromatic ring system. Aryl benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocyclic aromatic ring, cycloalkyl ring, or heterocycloalkyl ring. For example, aryl includes a phenyl ring fused to a 5- to 7-membered heterocycloalkyl ring containing one or more heteroatoms chosen from N, O, and S. For such fused, bicyclic ring systems wherein only one of the rings is a carbocyclic aromatic ring, the radical carbon atom may be at the carbocyclic aromatic ring or at the heterocycloalkyl ring. Examples of aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In certain embodiments, an aryl group can have from 6 to 20 carbon atoms ($C_{6-20}$), from 6 to 12 carbon atoms ($C_{6-12}$), from 6 to 10 carbon atoms ($C_{6-10}$), and in certain embodiments from 6 to 8 carbon atoms ($C_{6-8}$). Aryl, however, does not encompass or overlap in any way with heteroaryl, separately defined herein.

"Compounds" of Formula (I) disclosed herein include any specific compounds within the formula. Compounds may be identified either by their chemical structure and/or chemical name. Compounds are named using Accelrys Draw 4.1 SP1, version MDL.Draw.Editor 4.1. 100.70 (Accelrys, Inc., San Diego, Calif.). When the chemical structure and chemical name conflict, the chemical structure is determinative of the identity of the compound. The compounds described herein may comprise one or more chiral centers and/or double bonds and therefore may exist as stereoisomers such as double-bond isomers (i.e., geometric isomers), enantiomers, or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques or chiral synthesis techniques well known to the skilled artisan. Compounds of Formula (I) include, but are not limited to, optical isomers of compounds of Formula (I), racemates thereof, and other mixtures thereof. In such embodiments, a single enantiomer or diastereomer, i.e., optically active form can be obtained by asymmetric synthesis or by resolution of the racemates. Resolution of the racemates may be accomplished, for example, by conventional methods such as crystallization in the presence of a resolving agent, or chromatography using, for example, chiral stationary phases. Not withstanding the foregoing, in compounds of Formula (I) the configuration of the illustrated double bond is only in the E configuration (i.e. trans configuration).

Compounds of Formula (I) may also exist in several tautomeric forms including the enol form, the keto form, and mixtures thereof. Accordingly, the chemical structures depicted herein encompass all possible tautomeric forms of the illustrated compounds. Compounds of Formula (I) also include isotopically labeled compounds where one or more atoms have an atomic mass different from the atomic mass conventionally found in nature. Examples of isotopes that may be incorporated into the compounds disclosed herein include, but are not limited to, $^2H$, $^3H$, $^{11}C$, $^{13}C$, $^{14}C$, $^{15}N$, $^{18}O$ $^{17}O$, etc. Compounds may exist in unsolvated forms as well as solvated forms, including hydrated forms and as N-oxides. In general, compounds as referred to herein may be free acid, hydrated, solvated, or N-oxides. Certain compounds may exist in multiple crystalline, co-crystalline, or amorphous forms. Compounds of Formula (I) include pharmaceutically acceptable salts thereof, or pharmaceutically acceptable solvates of the free acid form of any of the foregoing, as well as crystalline forms of any of the foregoing.

Compounds of Formula (I) also include solvates. A solvate refers to a molecular complex of a compound with one or more solvent molecules in a stoichiometric or non-stoichiometric amount. Such solvent molecules are those commonly used in the pharmaceutical art, which are known to be innocuous to a patient, e.g., water, ethanol, and the like. A molecular complex of a compound or moiety of a compound and a solvent can be stabilized by non-covalent intra-molecular forces such as, for example, electrostatic forces, van der Waals forces, or hydrogen bonds. The term "hydrate" refers to a solvate in which the one or more solvent molecules is water.

Further, when partial structures of the compounds are illustrated, an asterisk (*) or a wavy line ( ~~~~ ) indicates the point of attachment of the partial structure to the rest of the molecule.

"Cycloalkyl" refers to a saturated or partially unsaturated cyclic alkyl radical. Where a specific level of saturation is intended, the nomenclature cycloalkanyl or cycloalkenyl is used. Examples of cycloalkyl groups include, but are not limited to, groups derived from cyclopropane, cyclobutane, cyclopentane, cyclohexane, and the like. In certain embodiments, a cycloalkyl group is $C_{3-15}$ cycloalkyl, $C_{3-12}$ cycloalkyl, and in certain embodiments, $C_{3-8}$ cycloalkyl.

"Disease" refers to a disease, disorder, condition, or symptom of any of the foregoing.

"Drug" as defined under 21 U.S.C. §321(g)(1) means "(A) articles recognized in the official United States Pharmacopoeia, official Homeopathic Pharmacopoeia of the United States, or official National Formulary, or any supplement to any of them; and (B) articles intended for use in the diagnosis, cure, mitigation, treatment, or prevention of disease in man or other animals; and (C) articles (other than food) intended to affect the structure or any function of the body of man or other animals . . . ."

"Halogen" refers to a fluoro, chloro, bromo, or iodo group. In certain embodiments, halogen refers to a chloro group.

"Heteroalkyl" by itself or as part of another substituent refers to an alkyl group in which one or more of the carbon atoms (and certain associated hydrogen atoms) are independently replaced with the same or different heteroatomic groups. Examples of heteroatomic groups include, but are not limited to, —O—, —S—, —O—O—, —S—S—, —O—S—, —NR$^{91}$, =N—N=, —N=N—, —N=N—NR$^{91}$—, —PR$^{91}$—, —P(O)$_2$—, —POR$^{91}$—, —O—P(O)$_2$—, —SO—, —SO$_2$—, —Sn(R$^{91}$)$_2$—, and the like, where each R$^{91}$ is independently chosen from hydrogen, $C_{1-6}$ alkyl, substituted $C_{1-6}$ alkyl, $C_{6-12}$ aryl, substituted $C_{6-12}$ aryl, $C_{7-18}$ arylalkyl, substituted $C_{7-18}$ arylalkyl, $C_{3-7}$ cycloalkyl, substituted $C_{3-7}$ cycloalkyl, $C_{3-7}$ heterocycloalkyl, substituted $C_{3-7}$ heterocycloalkyl, $C_{1-6}$ heteroalkyl, substituted $C_{1-6}$ heteroalkyl, $C_{6-12}$ heteroaryl, substituted $C_{6-12}$ heteroaryl, $C_{7-18}$ heteroarylalkyl, or substituted $C_{7-18}$ heteroarylalkyl. Reference to, for example, a $C_{1-6}$ heteroalkyl, means a $C_{1-6}$ alkyl group in which at least one of the carbon atoms (and certain associated hydrogen atoms) is replaced with a heteroatom. For example $C_{1-6}$ heteroalkyl includes groups having five carbon atoms and one heteroatom, groups having four carbon atoms and two heteroatoms, etc. In certain embodiments, each $R^{91}$ is independently chosen from hydrogen and $C_{1-3}$ alkyl. In certain embodiments, a heteroatomic group is chosen from —O—, —S—, —NH—, —N(CH$_3$)—, and —SO$_2$—; and in certain embodiments, the heteroatomic group is —O—.

"Heteroaryl" by itself or as part of another substituent refers to a aryl group in which one or more of the carbon atoms (and certain associated hydrogen atoms) are independently replaced with the same or different heteroatomic groups. Examples of heteroatomic groups include, but are not limited to, —O—, —S—, —O—O—, —S—S—, —O—S—, —NR$^{91}$, =N—N=, —N=N—, —N=N—NR$^{91}$—, —PR$^{91}$—, —P(O)$_2$—, —POR$^{91}$—, —O—P(O)$_2$—, —SO—, —SO$_2$—, —Sn(R$^{91}$)$_2$—, and the like, where each $R^{91}$ is independently chosen from hydrogen, $C_{1-6}$ alkyl, substituted $C_{1-6}$ alkyl, $C_{6-12}$ aryl, substituted $C_{6-12}$ aryl, $C_{7-18}$ arylalkyl, substituted $C_{7-18}$ arylalkyl, $C_{3-7}$ cycloalkyl, substituted $C_{3-7}$ cycloalkyl, $C_{3-7}$ heterocycloalkyl, substituted $C_{3-7}$ heterocycloalkyl, $C_{1-6}$ heteroalkyl, substituted $C_{1-6}$ heteroalkyl, $C_{6-12}$ heteroaryl, substituted $C_{6-12}$ heteroaryl, $C_{7-18}$ heteroarylalkyl, or substituted $C_{7-18}$ heteroarylalkyl.

Heteroaryl encompasses multiple ring systems having at least one heteroaromatic ring fused to at least one other ring, which can be aromatic or non-aromatic. For example, heteroaryl encompasses bicyclic rings in which one ring is heteroaromatic and the second ring is a heterocycloalkyl ring. For such fused, bicyclic heteroaryl ring systems wherein only one of the rings contains one or more heteroatoms, the radical carbon may be at the aromatic ring or at the heterocycloalkyl ring.

Examples of heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, thiazolidine, oxazolidine, and the like. In certain embodiments, a heteroaryl group is from 4- to 20-membered heteroaryl ($C_{4-20}$), and in certain embodiments from 4- to 12-membered heteroaryl ($C_{4-10}$). In certain embodiments, heteroaryl groups are those derived from thiophene, pyrrole, benzothiophene, benzofuran, indole, pyridine, quinoline, imidazole, oxazole, or pyrazine. For example, in certain embodiments, $C_5$ heteroaryl can be furyl, thienyl, pyrrolyl, imidazolyl, pyrazolyl, isothiazolyl, and isoxazolyl.

"Heterocycloalkyl" by itself or as part of another substituent refers to a cycloalkyl group in which one or more of the carbon atoms (and certain associated hydrogen atoms) are independently replaced with the same or different heteroatomic groups. Examples of heteroatomic groups include, but are not limited to, —O—, —S—, —O—O—, —S—S—, —O—S—, —NR$^{91}$, =N—N=, —N=N—, —N=N—NR$^{91}$—, —PR$^{91}$—, —P(O)$_2$—, —POR$^{91}$—, —O—P(O)$_2$—, —SO—, —SO$_2$—, —Sn(R$^{91}$)$_2$—, and the like, where each $R^{91}$ is independently chosen from hydrogen, $C_{1-6}$ alkyl, substituted $C_{1-6}$ alkyl, $C_{6-12}$ aryl, substituted $C_{6-12}$ aryl, $C_{7-18}$ arylalkyl, substituted $C_{7-18}$ arylalkyl, $C_{3-7}$ cycloalkyl, substituted $C_{3-7}$ cycloalkyl, $C_{3-7}$ heterocycloalkyl, substituted $C_{3-7}$ heterocycloalkyl, $C_{1-6}$ heteroalkyl, substituted $C_{1-6}$ heteroalkyl, $C_{6-12}$ heteroaryl, substituted $C_{6-12}$ heteroaryl, $C_{7-18}$ heteroarylalkyl, or substituted $C_{7-18}$ heteroarylalkyl. Reference to, for example, a $C_{3-6}$ heterocycloalkyl, means a $C_{3-6}$ cycloalkyl group in which at least one of the carbon atoms (and certain associated hydrogen atoms) is replaced with a heteroatom. For example $C_{3-6}$ heterocycloalkyl includes groups having five carbon atoms and one heteroatom, groups having four carbon atoms and two heteroatoms, etc. In certain embodiments, each $R^{91}$ is independently chosen from hydrogen and $C_{1-3}$ alkyl. In certain embodiments, a heteroatomic group is chosen from —O—, —S—, —NH—, —N(CH$_3$)—, and —SO$_2$—; and in certain embodiments, the heteroatomic group is —O—.

"Parent aromatic ring system" refers to an unsaturated cyclic or polycyclic ring system having a conjugated π (pi) electron system. Included within the definition of "parent aromatic ring system" are fused ring systems in which one or more of the rings are aromatic and one or more of the rings are saturated or unsaturated, such as, for example, fluorene, indane, indene, phenalene, etc. Examples of parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like.

"Parent heteroaromatic ring system" refers to an aromatic ring system in which one or more carbon atoms (and any associated hydrogen atoms) are independently replaced with the same or different heteroatom in such a way as to maintain the continuous π-electron system characteristic of aromatic systems and a number of out-of-plane π-electrons corresponding to the Hückel rule (4n+2). Examples of heteroatoms to replace the carbon atoms include, but are not limited to, N, P, O, S, and Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Examples of parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, thiazolidine, oxazolidine, and the like.

"Patient" refers to a mammal, for example, a human.

"Pharmaceutically acceptable" refers to approved or approvable by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound, which possesses the desired pharmacological activity of the parent compound. Such salts include acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; and salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine, and the like. In certain embodiments, a pharmaceutically acceptable salt is the hydrochloride salt. In certain embodiments, a pharmaceutically acceptable salt is the sodium salt.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which a compound provided by the present disclosure may be administered to a patient and which does not destroy the pharmacological activity thereof and which is non-toxic when administered in doses sufficient to provide a therapeutically effective amount of the compound.

"Pharmaceutical composition" refers to a compound of Formula (I) and at least one pharmaceutically acceptable vehicle, with which the compound of Formula (I) is administered to a patient.

"Substituted" refers to a group in which one or more hydrogen atoms are independently replaced with the same or substituent group(s). In certain embodiments, each substituent group is independently chosen from halogen, —OH, —CN, —CF$_3$, =O, —NO$_2$, benzyl, —C(O)NR$^{21}{}_2$, —R$^{21}$, —OR$^{21}$, —C(O)R$^{21}$, —COOR$^{21}$, —C(R$^{21}$)NH$_2$, —C(O)C(R$^{21}$)NH$_2$, —C(R$^{21}$)C(O)OH, —NC(R$^{21}$)C(O)OH, —NR$^{21}{}_2$, —NR$^{21}$C(O)R$^{21}$, and —O(O)R$^{21}$, wherein each R$^{21}$ is independently chosen from hydrogen, C$_{1-6}$ alkyl, C$_{1-6}$ heteroalkyl, C$_{3-12}$ cycloalkyl, C$_{5-10}$ aryl, and C$_{5-10}$ heteroaryl. In certain embodiments, each substituent group is independently chosen from halogen, —OH, —CN, —CF$_3$, —NO$_2$, benzyl, —R$^{21}$, —OR$^{21}$, —C(O)R$^{21}$, —COOR$^{21}$, —C(R$^{21}$)NH$_2$, —C(O)C(R$^{21}$)NH$_2$, —C(R$^{21}$)C(O)OH, —NC(R$^{21}$)C(O)OH, —NR$^{21}{}_2$, —NR$^{21}$C(O)R$^{21}$, and —O(O)R$^{21}$, wherein each R$^{21}$ is independently chosen from hydrogen, C$_{1-6}$ alkyl, C$_{1-6}$ heteroalkyl, C$_{3-12}$ cycloalkyl, C$_{5-10}$ aryl, and C$_{5-10}$ heteroaryl. In certain embodiments, each substituent group is independently chosen from halogen, —OH, —CN, —CF$_3$, =O, —NO$_2$, benzyl, —C(O)NR$^{21}{}_2$, —R$^{21}$, —OR$^{21}$, —C(O)R$^{21}$, —COOR$^{21}$, —NR$^{21}{}_2$, —NR$^{21}$C(O)R$^{21}$, and —O(O)R$^{21}$, wherein each R$^{21}$ is independently chosen from hydrogen, C$_{1-6}$ alkyl, C$_{1-6}$ heteroalkyl, C$_{3-12}$ cycloalkyl, C$_{5-10}$ aryl, and C$_{5-10}$ heteroaryl. In certain embodiments, each substituent group is independently chosen from —OH, —NH$_2$, and C$_{1-4}$ alkyl. In certain embodiments, each substituent group is independently chosen from —OH, —C(O)NR$^{21}{}_2$, —R$^{21}$, —C(O)R$^{21}$, —COOR$^{21}$, —C(R$^{21}$)NH$_2$, —C(O)C(R$^{21}$)NH$_2$, —C(R$^{21}$)C(O)OH, and —NC(R$^{21}$)C(O)OH, wherein each R$^{21}$ is independently chosen from a hydrogen, methyl, isopropyl, sec-butyl, phenyl, benzyl, p-hydroxybenzyl, 1H-imidazol-5-ylmethyl, 1H-indol-3-ylmethyl, —CH$_2$OH, —CH(OH)CH$_3$, —CH$_2$CH$_2$SCH$_3$, —CH$_2$CONH$_2$, —CH$_2$COOH, —CH$_2$CH$_2$CONH$_2$, —CH$_2$CH$_2$COOH, —(CH$_2$)$_3$NHC(=NH)NH$_2$, —(CH$_2$)$_3$NH$_2$, —(CH$_2$)$_3$NHCOCH$_3$, —(CH$_2$)$_3$NHCHO, —(CH$_2$)$_4$NHC(=NH)NH$_2$, —(CH$_2$)$_4$NH$_2$, —(CH$_2$)$_4$NHCOCH$_3$, —(CH$_2$)$_4$NHCHO, —(CH$_2$)$_3$NHCONH$_2$, —(CH$_2$)$_4$NHCONH$_2$, and —CH$_2$CH$_2$CH(OH)CH$_2$NH$_2$.

"Treating" or "treatment" of any disease refers to reversing, alleviating, arresting, or ameliorating a disease or at least one of the clinical symptoms of a disease, reducing the risk of acquiring a disease or at least one of the clinical symptoms of a disease, inhibiting the progress of a disease or at least one of the clinical symptoms of the disease or reducing the risk of developing a disease or at least one of the clinical symptoms of a disease. "Treating" or "treatment" also refers to inhibiting the disease, either physically, (e.g., stabilization of a discernible symptom), physiologically, (e.g., stabilization of a physical parameter), or both, and to inhibiting at least one physical parameter that may or may not be discernible to the patient. In certain embodiments, "treating" or "treatment" refers to delaying the onset of the disease or at least one or more symptoms thereof in a patient which may be exposed to or predisposed to a disease even though that patient does not yet experience or display symptoms of the disease.

"Therapeutically effective amount" refers to the amount of a compound that, when administered to a subject for treating a disease, or at least one of the clinical symptoms of a disease, is sufficient to affect such treatment of the disease or symptom thereof. The "therapeutically effective amount" may vary depending, for example, on the compound, the disease and/or symptoms of the disease, severity of the disease and/or symptoms of the disease or disorder, the age, weight, and/or health of the patient to be treated, and the judgment of the prescribing physician. An appropriate amount in any given instance may be ascertained by those skilled in the art or capable of determination by routine experimentation.

"Therapeutically effective dose" refers to a dose that provides effective treatment of a disease or disorder in a patient. A therapeutically effective dose may vary from compound to compound, and from patient to patient, and may depend upon factors such as the condition of the patient and the route of delivery. A therapeutically effective dose may be determined in accordance with routine pharmacological procedures known to those skilled in the art.

Reference is now made in detail to certain embodiments of compounds, compositions, and methods. The disclosed embodiments are not intended to be limiting of the claims. To the contrary, the claims are intended to cover all alternatives, modifications, and equivalents.

Compounds

Certain embodiments provide a compound of Formula (I):

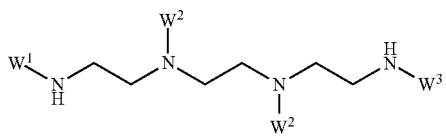

or a pharmaceutically acceptable salt thereof, wherein:
$W^1$ is chosen from substituents of Formula (I-a) and Formula (I-b); and
each $W^2$ and $W^3$ is independently chosen from hydrogen and substituents of Formula (I-a) and Formula (I-b):

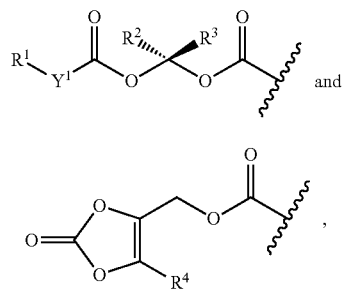

wherein
$R^1$, $R^2$, $R^3$, and $R^4$ are independently chosen from hydrogen, $C_{1-6}$ alkyl, $C_{1-6}$ heteroalkyl, $C_{3-12}$ cycloalkyl, $C_{3-12}$ heterocycloalkyl, $C_{5-10}$ aryl, and $C_{5-10}$ heteroaryl; and
$Y^1$ is chosen from a bond and —O—.

In certain embodiments of a compound of Formula (I), $W^1$ is chosen from substituents of Formula (I-a) and Formula (I-b).

In certain embodiments of a compound of Formula (I), $W^1$ is chosen from the substituent of Formula (I-a), wherein $R^1$, $R^2$, and $R^3$ are independently chosen from hydrogen, methyl, ethyl, n-propyl, isopropyl, tert-butyl, cyclohexyl, phenyl, and benzyl; and $Y^1$ is chosen from a bond and —O—.

In certain embodiments of a compound of Formula (I), $W^1$ is chosen from the substituent of Formula (I-a), wherein $R^1$, $R^2$, and $R^3$ are independently chosen from hydrogen, methyl, ethyl, isopropyl, tert-butyl, cyclohexyl, phenyl, and benzyl; and $Y^1$ is a bond.

In certain embodiments of a compound of Formula (I), $W^1$ is chosen from the substituent of Formula (I-a), wherein $R^1$ is chosen from methyl, ethyl, isopropyl, tert-butyl, cyclohexyl, phenyl, and benzyl; $R^2$ and $R^3$ are chosen from hydrogen and methyl; and $Y^1$ is a bond.

In certain embodiments of a compound of Formula (I), $W^1$ is chosen from the substituent of Formula (I-a), wherein $R^1$ is chosen from methyl, ethyl, isopropyl, tert-butyl, cyclohexyl, phenyl, and benzyl; $R^2$ and $R^3$ are hydrogen; and $Y^1$ is a bond.

In certain embodiments of a compound of Formula (I), $W^1$ is chosen from the substituent of Formula (I-a), wherein $R^1$ is methyl, $R^2$ and $R^3$ are hydrogen, and $Y^1$ is a bond.

In certain embodiments of a compound of Formula (I), $W^1$ is chosen from the substituent of Formula (I-a), wherein $R^1$ is ethyl, $R^2$ and $R^3$ are hydrogen, and $Y^1$ is a bond.

In certain embodiments of a compound of Formula (I), $W^1$ is chosen from the substituent of Formula (I-a), wherein $R^1$ is n-propyl, $R^2$ and $R^3$ are hydrogen, and $Y^1$ is a bond.

In certain embodiments of a compound of Formula (I), $W^1$ is chosen from the substituent of Formula (I-a), wherein $R^1$ is isopropyl, $R^2$ and $R^3$ are hydrogen, and $Y^1$ is a bond.

In certain embodiments of a compound of Formula (I), $W^1$ is chosen from the substituent of Formula (I-a), wherein $R^1$ is tert-butyl, $R^2$ and $R^3$ are hydrogen, and $Y^1$ is a bond.

In certain embodiments of a compound of Formula (I), $W^1$ is chosen from the substituent of Formula (I-a), wherein $R^1$ is cyclohexyl, $R^2$ and $R^3$ are hydrogen, and $Y^1$ is a bond.

In certain embodiments of a compound of Formula (I), $W^1$ is chosen from the substituent of Formula (I-a), wherein $R^1$ is phenyl, $R^2$ and $R^3$ are hydrogen, and $Y^1$ is a bond.

In certain embodiments of a compound of Formula (I), $W^1$ is chosen from the substituent of Formula (I-a), wherein $R^1$ is benzyl, $R^2$ and $R^3$ are hydrogen, and $Y^1$ is a bond.

In certain embodiments of a compound of Formula (I), $W^1$ is chosen from the substituent of Formula (I-b), wherein $R^4$ is chosen from methyl, ethyl, n-propyl, isopropyl, tert-butyl, cyclohexyl, phenyl, and benzyl.

In certain embodiments of a compound of Formula (I), $W^1$ is chosen from the substituent of Formula (I-b), wherein $R^4$ is methyl.

In certain embodiments of a compound of Formula (I), $W^1$ is chosen from the substituent of Formula (I-b), wherein $R^4$ is phenyl.

In certain embodiments of a compound of Formula (I), each $W^2$ and $W^3$ is independently chosen from hydrogen and substituents of Formula (I-a) and Formula (I-b).

In certain embodiments of a compound of Formula (I), each $W^2$ and $W^3$ is independently chosen from hydrogen and the substituent of Formula (I-a), wherein $R^1$, $R^2$, and $R^3$ are independently chosen from hydrogen, methyl, ethyl, n-propyl, isopropyl, tert-butyl, cyclohexyl, phenyl, and benzyl; and $Y^1$ is chosen from a bond and —O—.

In certain embodiments of a compound of Formula (I), each $W^2$ and $W^3$ is independently chosen from hydrogen and the substituent of Formula (I-a), wherein $R^1$, $R^2$, and $R^3$ are independently chosen from hydrogen, methyl, ethyl, isopropyl, tert-butyl, cyclohexyl, phenyl, and benzyl; and $Y^1$ is a bond.

In certain embodiments of a compound of Formula (I each $W^2$ and $W^3$ is independently chosen from hydrogen and the substituent of Formula (I-a), wherein $R^1$ is chosen from methyl, ethyl, isopropyl, tert-butyl, cyclohexyl, phenyl, and benzyl; $R^2$ and $R^3$ are chosen from hydrogen and methyl; and $Y^1$ is a bond.

In certain embodiments of a compound of Formula (I), each $W^2$ and $W^3$ is independently chosen from hydrogen and the substituent of Formula (I-a), wherein $R^1$ is chosen from methyl, ethyl, isopropyl, tert-butyl, cyclohexyl, phenyl, and benzyl; $R^2$ and $R^3$ are hydrogen; and $Y^1$ is a bond.

In certain embodiments of a compound of Formula (I), each $W^2$ and $W^3$ is independently chosen from hydrogen and the substituent of Formula (I-a), wherein $R^1$ is methyl, $R^2$ and $R^3$ are hydrogen, and $Y^1$ is a bond.

In certain embodiments of a compound of Formula (I), each $W^2$ and $W^3$ is independently chosen from hydrogen and the substituent of Formula (I-a), wherein $R^1$ is ethyl, $R^2$ and $R^3$ are hydrogen, and $Y^1$ is a bond.

In certain embodiments of a compound of Formula (I), each $W^2$ and $W^3$ is independently chosen from hydrogen and the substituent of Formula (I-a), wherein $R^1$ is n-propyl, $R^2$ and $R^3$ are hydrogen, and $Y^1$ is a bond.

In certain embodiments of a compound of Formula (I), each $W^2$ and $W^3$ is independently chosen from hydrogen and the substituent of Formula (I-a), wherein $R^1$ is isopropyl, $R^2$ and $R^3$ are hydrogen, and $Y^1$ is a bond.

In certain embodiments of a compound of Formula (I), each $W^2$ and $W^3$ is independently chosen from hydrogen and the substituent of Formula (I-a), wherein $R^1$ is tert-butyl, $R^2$ and $R^3$ are hydrogen, and $Y^1$ is a bond.

In certain embodiments of a compound of Formula (I), each $W^2$ and $W^3$ is independently chosen from hydrogen and the substituent of Formula (I-a), wherein $R^1$ is cyclohexyl, $R^2$ and $R^3$ are hydrogen, and $Y^1$ is a bond.

In certain embodiments of a compound of Formula (I), each $W^2$ and $W^3$ is independently chosen from hydrogen and the substituent of Formula (I-a), wherein $R^1$ is phenyl, $R^2$ and $R^3$ are hydrogen, and $Y^1$ is a bond.

In certain embodiments of a compound of Formula (I), each $W^2$ and $W^3$ is independently chosen from hydrogen and the substituent of Formula (I-a), wherein $R^1$ is benzyl, $R^2$ and $R^3$ are hydrogen, and $Y^1$ is a bond.

In certain embodiments of a compound of Formula (I), each $W^2$ and $W^3$ is independently chosen from hydrogen and the substituent of Formula (I-b), wherein $R^4$ is chosen from methyl, ethyl, n-propyl, isopropyl, tert-butyl, cyclohexyl, phenyl, and benzyl.

In certain embodiments of a compound of Formula (I), each $W^2$ and $W^3$ is independently chosen from hydrogen and the substituent of Formula (I-b), wherein $R^4$ is methyl.

In certain embodiments of a compound of Formula (I), each $W^2$ and $W^3$ is independently chosen from hydrogen and the substituent of Formula (I-b), wherein $R^4$ is phenyl.

In certain embodiments of a compound of Formula (I), $W^1$ is chosen from a compound of Formula (I-a) and Formula (I-b); and each $W^2$ and $W^3$ is independently chosen from hydrogen and substituent of Formula (I-a) and Formula (I-b).

In certain embodiments of a compound of Formula (I), $W^1$ is chosen from substituents of Formula (I-a) and Formula (I-b); and each $W^2$ and $W^3$ is independently chosen from hydrogen and substituent of Formula (I-a) and Formula (I-b); wherein $R^1$, $R^2$, $R^3$, and $R^4$ are independently chosen from hydrogen, methyl, ethyl, n-propyl, isopropyl, tert-butyl, cyclohexyl, phenyl, and benzyl; and $Y^1$ is chosen from a bond and —O—.

In certain embodiments of a compound of Formula (I), $W^1$ is chosen from substituents of Formula (I-a) and Formula (I-b); and each $W^2$ and $W^3$ is independently chosen from hydrogen and substituents of Formula (I-a) and Formula (I-b); wherein $R^1$, $R^2$, $R^3$, and $R^4$ are independently chosen from hydrogen, methyl, ethyl, n-propyl, isopropyl, tert-butyl, cyclohexyl, phenyl, and benzyl; and $Y^1$ is a bond.

In certain embodiments of a compound of Formula (I), $W^1$ and $W^3$ are the substituent of Formula (I-a); and each $W^2$ is hydrogen; wherein $R^1$ is methyl, $R^2$ and $R^3$ are hydrogen, and $Y^1$ is a bond.

In certain embodiments of a compound of Formula (I), $W^1$ and $W^3$ are the substituent of Formula (I-a); and each $W^2$ is hydrogen; wherein $R^1$ is ethyl, $R^2$ and $R^3$ are hydrogen, and $Y^1$ is a bond.

In certain embodiments of a compound of Formula (I), $W^1$ and $W^3$ are the substituent of Formula (I-a); and each $W^2$ is hydrogen; wherein $R^1$ is n-propyl, $R^2$ and $R^3$ are hydrogen, and $Y^1$ is a bond.

In certain embodiments of a compound of Formula (I), $W^1$ and $W^3$ are the substituent of Formula (I-a); and each $W^2$ is hydrogen; wherein $R^1$ is isopropyl, $R^2$ and $R^3$ are hydrogen, and $Y^1$ is a bond.

In certain embodiments of a compound of Formula (I), $W^1$ and $W^3$ are the substituent of Formula (I-a); and each $W^2$ is hydrogen; wherein $R^1$ is tert-butyl, $R^2$ and $R^3$ are hydrogen, and $Y^1$ is a bond.

In certain embodiments of a compound of Formula (I), $W^1$ and $W^3$ are the substituent of Formula (I-a); and each $W^2$ is hydrogen; wherein $R^1$ is cyclohexyl, $R^2$ and $R^3$ are hydrogen, and $Y^1$ is a bond.

In certain embodiments of a compound of Formula (I), $W^1$ and $W^2$ are the substituent of Formula (I-a); and each $W^2$ is hydrogen; wherein $R^1$ is phenyl, $R^2$ and $R^3$ are hydrogen, and $Y^1$ is a bond.

In certain embodiments of a compound of Formula (I), $W^1$ and $W^3$ are the substituent of Formula (I-a); and each $W^2$ is hydrogen; wherein $R^1$ is benzyl, $R^2$ and $R^3$ are hydrogen, and $Y^1$ is a bond.

In certain embodiments of a compound of Formula (I), $W^1$ and $W^3$ are the substituent of Formula (I-a); and each $W^2$ is hydrogen; wherein $R^1$ is methyl, $R^2$ is hydrogen, $R^3$ is methyl, and $Y^1$ is a bond.

In certain embodiments of a compound of Formula (I), $W^1$ and $W^3$ are the substituent of Formula (I-a); and each $W^2$ is hydrogen; wherein $R^1$ is ethyl, $R^2$ is hydrogen, $R^3$ is methyl, and $Y^1$ is a bond.

In certain embodiments of a compound of Formula (I), $W^1$ and $W^3$ are the substituent of Formula (I-a); and each $W^2$ is hydrogen; wherein $R^1$ is n-propyl, $R^2$ is hydrogen, $R^3$ is methyl, and $Y^1$ is a bond.

In certain embodiments of a compound of Formula (I), $W^1$ and $W^3$ are the substituent of Formula (I-a); and each $W^2$ is hydrogen; wherein $R^1$ is isopropyl, $R^2$ is hydrogen, $R^3$ is methyl, and $Y^1$ is a bond.

In certain embodiments of a compound of Formula (I), $W^1$ and $W^3$ are the substituent of Formula (I-a); and each $W^2$ is hydrogen; wherein $R^1$ is tert-butyl, $R^2$ is hydrogen, $R^3$ is methyl, and $Y^1$ is a bond.

In certain embodiments of a compound of Formula (I), $W^1$ and $W^3$ are the substituent of Formula (I-a); and each $W^2$ is hydrogen; wherein $R^1$ is cyclohexyl, $R^2$ is hydrogen, $R^3$ is methyl, and $Y^1$ is a bond.

In certain embodiments of a compound of Formula (I), $W^1$ and $W^3$ are the substituent of Formula (I-a); and each $W^2$ is hydrogen; wherein $R^1$ is phenyl, $R^2$ is hydrogen, $R^3$ is methyl, and $Y^1$ is a bond.

In certain embodiments of a compound of Formula (I), $W^1$ and $W^3$ are the substituent of Formula (I-a); and each $W^2$ is hydrogen; wherein $R^1$ is benzyl, $R^2$ is hydrogen, $R^3$ is methyl, and $Y^1$ is a bond.

In certain embodiments of a compound of Formula (I), $W^1$ and $W^3$ are the substituent of Formula (I-a); and each $W^2$ is hydrogen; wherein $R^1$ is methyl, $R^2$ is methyl, $R^3$ is hydrogen, and $Y^1$ is a bond.

In certain embodiments of a compound of Formula (I), $W^1$ and $W^3$ are the substituent of Formula (I-a); and each $W^2$ is hydrogen; wherein $R^1$ is ethyl, $R^2$ is methyl, $R^3$ is hydrogen, and $Y^1$ is a bond.

In certain embodiments of a compound of Formula (I), $W^1$ and $W^3$ are the substituent of Formula (I-a); and each $W^2$ is hydrogen; wherein $R^1$ is n-propyl, $R^2$ is methyl, $R^3$ is hydrogen, and $Y^1$ is a bond.

In certain embodiments of a compound of Formula (I), $W^1$ and $W^3$ are the substituent of Formula (I-a); and each $W^2$ is hydrogen; wherein $R^1$ is isopropyl, $R^2$ is methyl, $R^3$ is hydrogen, and $Y^1$ is a bond.

In certain embodiments of a compound of Formula (I), $W^1$ and $W^3$ are the substituent of Formula (I-a); and each $W^2$ is hydrogen; wherein $R^1$ is tert-butyl, $R^2$ is methyl, $R^3$ is hydrogen, and $Y^1$ is a bond.

In certain embodiments of a compound of Formula (I), $W^1$ and $W^3$ are the substituent of Formula (I-a); and each $W^2$ is hydrogen; wherein $R^1$ is cyclohexyl, $R^2$ is methyl, $R^3$ is hydrogen, and $Y^1$ is a bond.

In certain embodiments of a compound of Formula (I), $W^1$ and $W^3$ are the substituent of Formula (I-a); and each $W^2$ is hydrogen; wherein $R^1$ is phenyl, $R^2$ is methyl, $R^3$ is hydrogen, and $Y^1$ is a bond.

In certain embodiments of a compound of Formula (I), $W^1$ and $W^3$ are the substituent of Formula (I-a); and each $W^2$ is hydrogen; wherein $R^1$ is benzyl, $R^2$ is methyl, $R^3$ is hydrogen, and $Y^1$ is a bond.

In certain embodiments of a compound of Formula (I), the compound is chosen from a compound of Formula (I-A-1), Formula (I-A-2), Formula (I-A-3), Formula (I-A-4), Formula (I-A-5), Formula (I-A-6), Formula (I-A-7), Formula (I-A-8), Formula (I-A-9), Formula (I-A-10), Formula (I-A-11), Formula (I-A-12), Formula (I-A-13), Formula (I-A-14), Formula (I-A-15), Formula (I-A-16), Formula (I-A-17), Formula (I-A-18), Formula (I-A-19), Formula (I-A-20), Formula (I-A-21), Formula (I-A-22), Formula (I-A-23), Formula (I-A-24), Formula (I-A-25), Formula (I-A-26), Formula (I-A-27), Formula (I-A-28), Formula (I-A-29), Formula (I-A-30), Formula (I-A-31), and Formula (I-A-32), or a pharmaceutically acceptable salt of any of the foregoing:

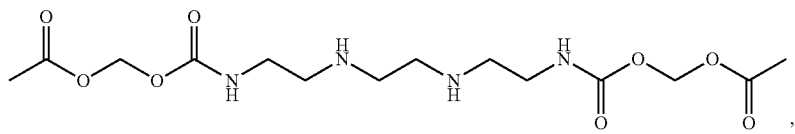

(I-A-1)

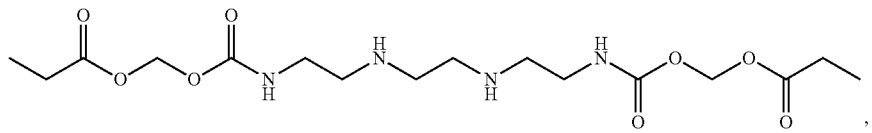

(I-A-2)

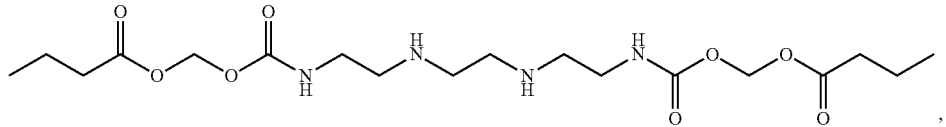

(I-A-3)

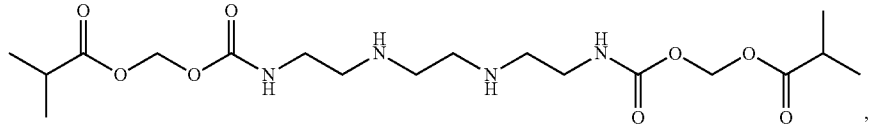

(I-A-4)

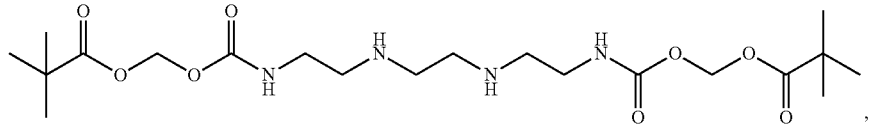

(I-A-5)

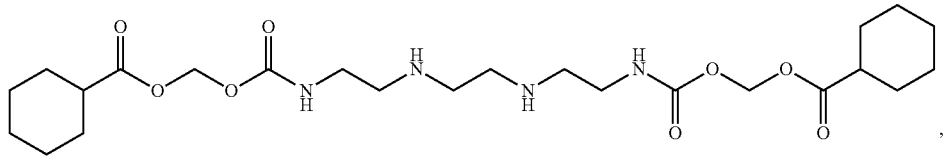

(I-A-6)

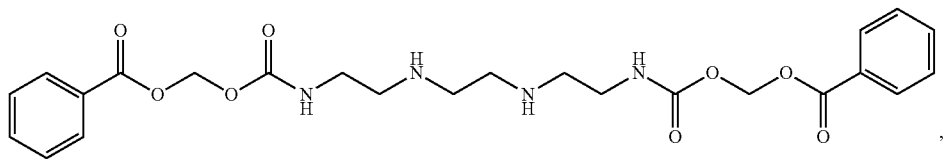

(I-A-7)

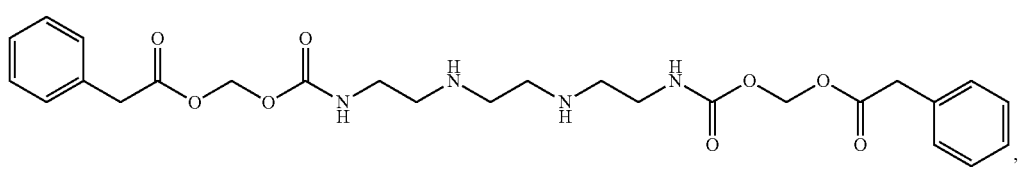

(I-A-8)

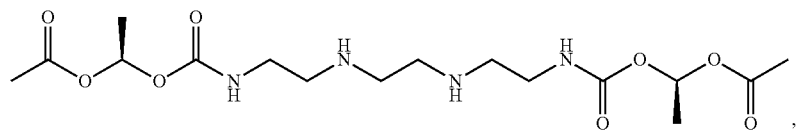
(I-A-9)
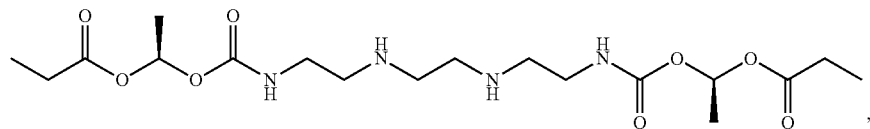
(I-A-10)
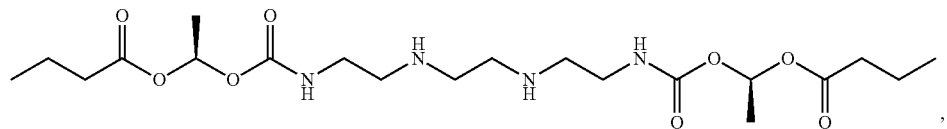
(I-A-11)
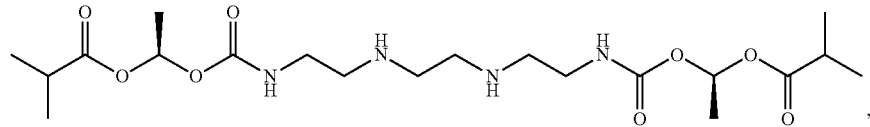
(I-A-12)
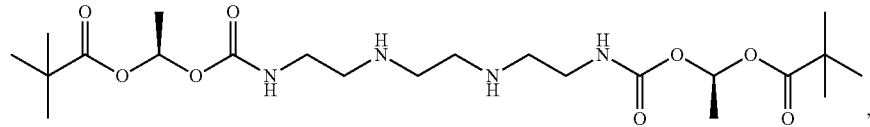
(I-A-13)
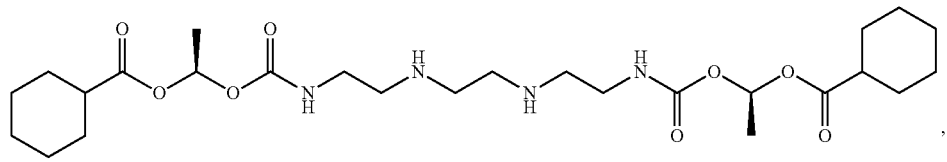
(I-A-14)
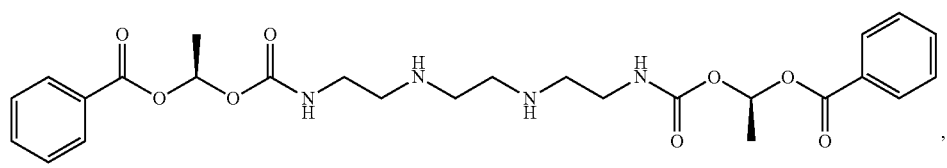
(I-A-15)
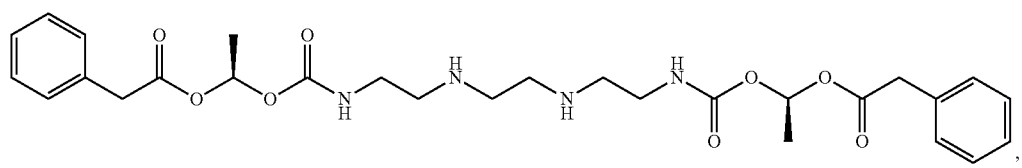
(I-A-16)
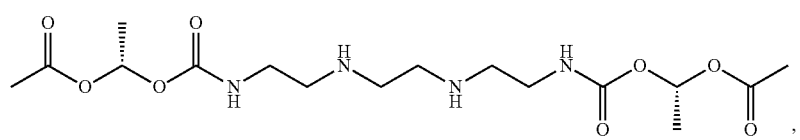
(I-A-17)
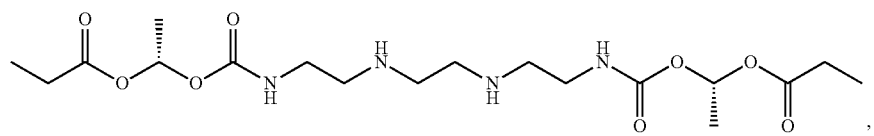
(I-A-18)

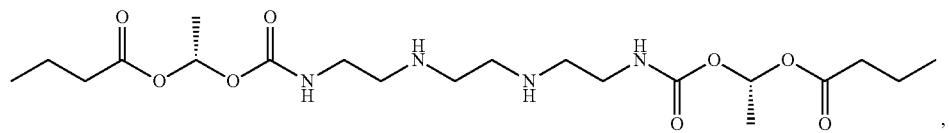
(I-A-19)
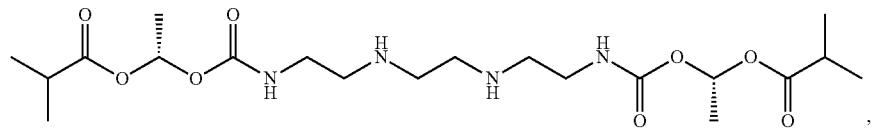
(I-A-20)
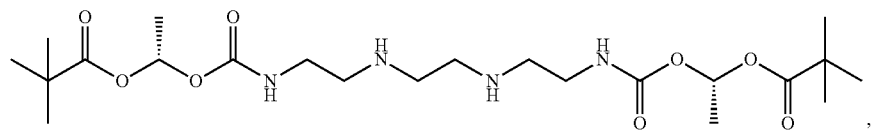
(I-A-21)
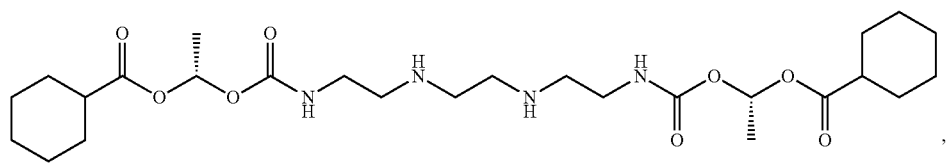
(I-A-22)
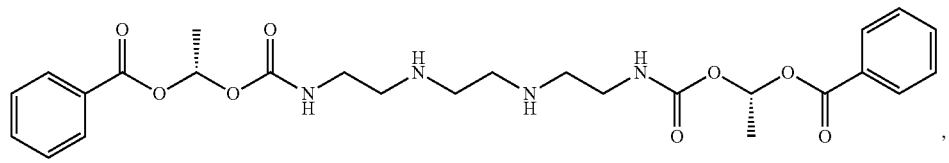
(I-A-23)
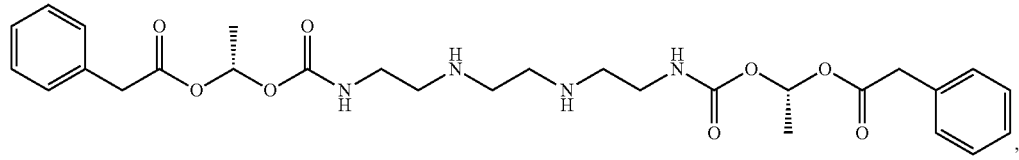
(I-A-24)
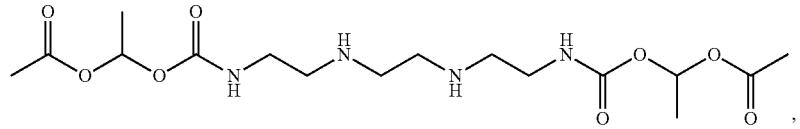
(I-A-25)
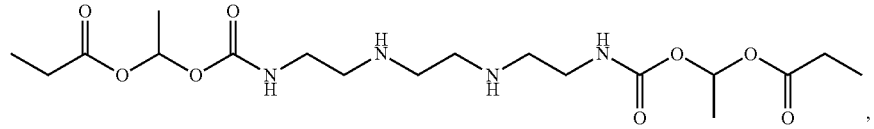
(I-A-26)
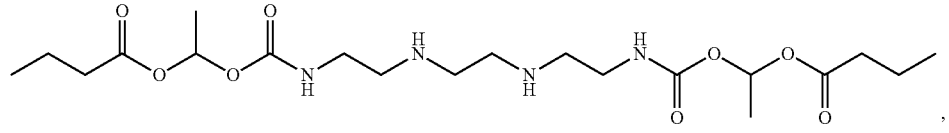
(I-A-27)
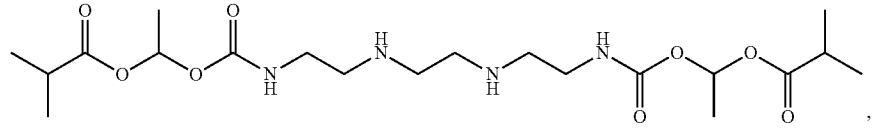
(I-A-28)

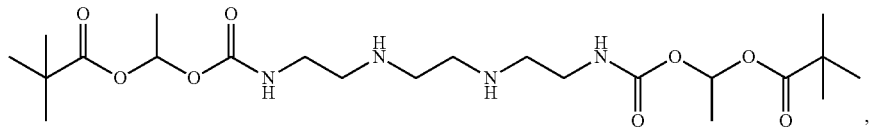
(I-A-29)

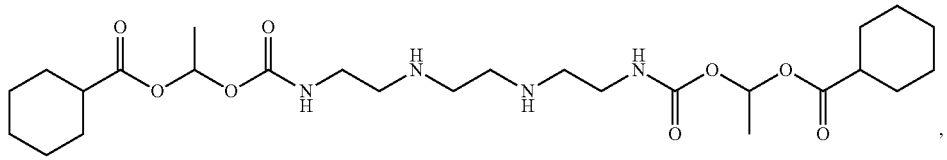
(I-A-30)

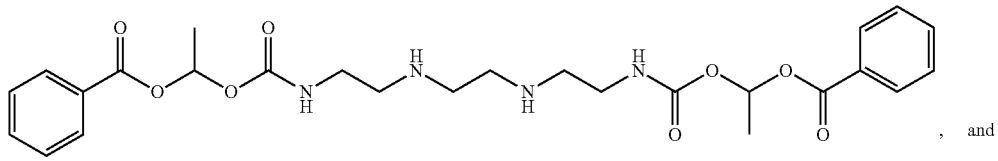
(I-A-31)

, and

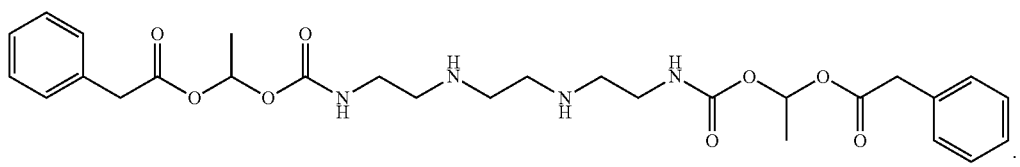
(I-A-32)

.

In certain embodiments of a compound of Formula (I), $W^1$ is the substituent of Formula (I-a); and each $W^2$ and $W^3$ is hydrogen; wherein $R^1$ is methyl, $R^2$ and $R^3$ are hydrogen, and $Y^1$ is a bond.

In certain embodiments of a compound of Formula (I), $W^1$ is the substituent of Formula (I-a); and each $W^2$ and $W^3$ is hydrogen; wherein $R^1$ is ethyl, $R^2$ and $R^3$ are hydrogen, and $Y^1$ is a bond.

In certain embodiments of a compound of Formula (I), $W^1$ is the substituent of Formula (I-a); and each $W^2$ and $W^3$ is hydrogen; wherein $R^1$ is n-propyl, $R^2$ and $R^3$ are hydrogen, and $Y^1$ is a bond.

In certain embodiments of a compound of Formula (I), $W^1$ is the substituent of Formula (I-a); and each $W^2$ and $W^3$ is hydrogen; wherein $R^1$ is isopropyl, $R^2$ and $R^3$ are hydrogen, and $Y^1$ is a bond.

In certain embodiments of a compound of Formula (I), $W^1$ is the substituent of Formula (I-a); and each $W^2$ and $W^3$ is hydrogen; wherein $R^1$ is tert-butyl, $R^2$ and $R^3$ are hydrogen, and $Y^1$ is a bond.

In certain embodiments of a compound of Formula (I), $W^1$ is the substituent of Formula (I-a); and each $W^2$ and $W^3$ is hydrogen; wherein $R^1$ is cyclohexyl, $R^2$ and $R^3$ are hydrogen, and $Y^1$ is a bond.

In certain embodiments of a compound of Formula (I), $W^1$ is the substituent of Formula (I-a); and each $W^2$ and $W^3$ is hydrogen; wherein $R^1$ is phenyl, $R^2$ and $R^3$ are hydrogen, and $Y^1$ is a bond.

In certain embodiments of a compound of Formula (I), $W^1$ is the substituent of Formula (I-a); and each $W^2$ and $W^3$ is hydrogen; wherein $R^1$ is benzyl, $R^2$ and $R^3$ are hydrogen, and $Y^1$ is a bond.

In certain embodiments of a compound of Formula (I), $W^1$ is the substituent of Formula (I-a); and each $W^2$ and $W^3$ is hydrogen; wherein $R^1$ is methyl, $R^2$ is hydrogen, $R^3$ is methyl, and $Y^1$ is a bond.

In certain embodiments of a compound of Formula (I), $W^1$ is the substituent of Formula (I-a); and each $W^2$ and $W^3$ is hydrogen; wherein $R^1$ is ethyl, $R^2$ is hydrogen, $R^3$ is methyl, and $Y^1$ is a bond.

In certain embodiments of a compound of Formula (I), $W^1$ is the substituent of Formula (I-a); and each $W^2$ and $W^3$ is hydrogen; wherein $R^1$ is n-propyl, $R^2$ is hydrogen, $R^3$ is methyl, and $Y^1$ is a bond.

In certain embodiments of a compound of Formula (I), $W^1$ is the substituent of Formula (I-a); and each $W^2$ and $W^3$ is hydrogen; wherein $R^1$ is isopropyl, $R^2$ is hydrogen, $R^3$ is methyl, and $Y^1$ is a bond.

In certain embodiments of a compound of Formula (I), $W^1$ is the substituent of Formula (I-a); and each $W^2$ and $W^3$ is hydrogen; wherein $R^1$ is tert-butyl, $R^2$ is hydrogen, $R^3$ is methyl, and $Y^1$ is a bond.

In certain embodiments of a compound of Formula (I), $W^1$ is the substituent of Formula (I-a); and each $W^2$ and $W^3$ is hydrogen; wherein $R^1$ is cyclohexyl, $R^2$ is hydrogen, $R^3$ is methyl, and $Y^1$ is a bond.

In certain embodiments of a compound of Formula (I), $W^1$ is the substituent of Formula (I-a); and each $W^2$ and $W^3$ is hydrogen; wherein $R^1$ is phenyl, $R^2$ is hydrogen, $R^3$ is methyl, and $Y^1$ is a bond.

In certain embodiments of a compound of Formula (I), $W^1$ is the substituent of Formula (I-a); and each $W^2$ and $W^3$ is hydrogen; wherein $R^1$ is benzyl, $R^2$ is hydrogen, $R^3$ is methyl, and $Y^1$ is a bond.

In certain embodiments of a compound of Formula (I), $W^1$ is the substituent of Formula (I-a); and each $W^2$ and $W^3$ is hydrogen; wherein $R^1$ is methyl, $R^2$ is methyl, $R^3$ is hydrogen, and $Y^1$ is a bond.

In certain embodiments of a compound of Formula (I), $W^1$ is the substituent of Formula (I-a); and each $W^2$ and $W^3$ is hydrogen; wherein $R^1$ is ethyl, $R^2$ is methyl, $R^3$ is hydrogen, and $Y^1$ is a bond.

In certain embodiments of a compound of Formula (I), W¹ is the substituent of Formula (I-a); and each W² and W³ is hydrogen; wherein R¹ is n-propyl, R² is methyl, R³ is hydrogen, and Y¹ is a bond.

In certain embodiments of a compound of Formula (I), W¹ is the substituent of Formula (I-a); and each W² and W³ is hydrogen; wherein R¹ is isopropyl, R² is methyl, R³ is hydrogen, and Y¹ is a bond.

In certain embodiments of a compound of Formula (I), W¹ is the substituent of Formula (I-a); and each W² and W³ is hydrogen; wherein R¹ is tert-butyl, R² is methyl, R³ is hydrogen, and Y¹ is a bond.

In certain embodiments of a compound of Formula (I), W¹ is the substituent of Formula (I-a); and each W² and W³ is hydrogen; wherein R¹ is cyclohexyl, R² is methyl, R³ is hydrogen, and Y¹ is a bond.

In certain embodiments of a compound of Formula (I), W¹ is the substituent of Formula (I-a); and each W² and W³ is hydrogen; wherein R¹ is phenyl, R² is methyl, R³ is hydrogen, and Y¹ is a bond.

In certain embodiments of a compound of Formula (I), W¹ is the substituent of Formula (I-a); and each W² and W³ is hydrogen; wherein R¹ is benzyl, R² is methyl, R³ is hydrogen, and Y¹ is a bond.

In certain embodiments of a compound of Formula (I), the compound is chosen from a compound of Formula (I-B-1), Formula (I-B-2), Formula (I-B-3), Formula (I-B-4), Formula (I-B-5), Formula (I-B-6), Formula (I-B-7), Formula (I-B-8), Formula (I-B-9), Formula (I-B-10), Formula (I-B-11), Formula (I-B-12), Formula (I-B-13), Formula (I-B-14), Formula (I-B-15), Formula (I-B-16), Formula (I-B-17), Formula (I-B-18), Formula (I-B-19), Formula (I-B-20), Formula (I-B-21), Formula (I-B-22), Formula (I-B-23), Formula (I-B-24), Formula (I-B-25), Formula (I-B-26), Formula (I-B-27), Formula (I-B-28), Formula (I-B-29), Formula (I-B-30), Formula (I-B-31), and Formula (I-B-32), or a pharmaceutically acceptable salt of any of the foregoing:

-continued (I-B-17) 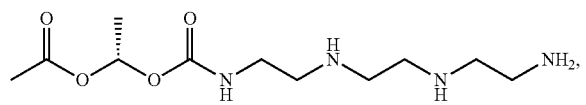

(I-B-18) 

(I-B-19) 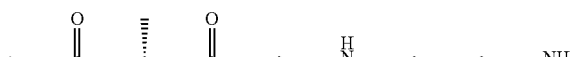

(I-B-20) 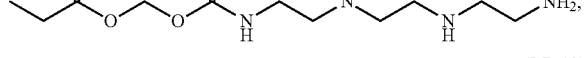

(I-B-21) 

(I-B-22) 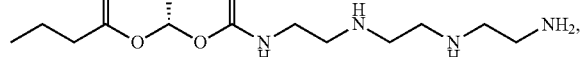

(I-B-23) 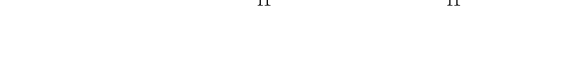

(I-B-24) 

(I-B-25) 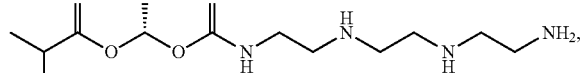

(I-B-26) 

(I-B-27) 

-continued (I-B-28) 

(I-B-29) 

(I-B-30) 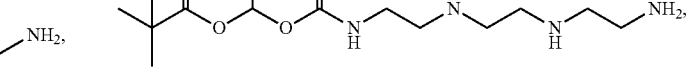

(I-B-31) 

and (I-B-32) 

In certain embodiments of a compound of Formula (I), each $W^1$, $W^2$, and $W^3$ is the substituent of Formula (I-a); wherein $R^1$ is methyl, $R^2$ and $R^3$ are hydrogen, and $Y^1$ is a bond.

In certain embodiments of a compound of Formula (I), each $W^1$, $W^2$, and $W^3$ is the substituent of Formula (I-a); wherein $R^1$ is ethyl, $R^2$ and $R^3$ are hydrogen, and $Y^1$ is a bond.

In certain embodiments of a compound of Formula (I), each $W^1$, $W^2$, and $W^3$ is the substituent of Formula (I-a); wherein $R^1$ is n-propyl, $R^2$ and $R^3$ are hydrogen, and $Y^1$ is a bond.

In certain embodiments of a compound of Formula (I), each $W^1$, $W^2$, and $W^3$ is the substituent of Formula (I-a); wherein $R^1$ is isopropyl, $R^2$ and $R^3$ are hydrogen, and $Y^1$ is a bond.

In certain embodiments of a compound of Formula (I), each $W^1$, $W^2$, and $W^3$ is the substituent of Formula (I-a); wherein $R^1$ is tert-butyl, $R^2$ and $R^3$ are hydrogen, and $Y^1$ is a bond.

In certain embodiments of a compound of Formula (I), each $W^1$, $W^2$, and $W^3$ is the substituent of Formula (I-a); wherein $R^1$ is cyclohexyl, $R^2$ and $R^3$ are hydrogen, and $Y^1$ is a bond.

In certain embodiments of a compound of Formula (I), each $W^1$, $W^2$, and $W^3$ is the substituent of Formula (I-a); wherein $R^1$ is phenyl, $R^2$ and $R^3$ are hydrogen, and $Y^1$ is a bond.

In certain embodiments of a compound of Formula (I), each $W^1$, $W^2$, and $W^3$ is the substituent of Formula (I-a); wherein $R^1$ is benzyl, $R^2$ and $R^3$ are hydrogen, and $Y^1$ is a bond.

In certain embodiments of a compound of Formula (I), the compound is chosen from a compound of Formula (I-C-1), Formula (I-C-2), Formula (I-C-3), Formula (I-C-4), Formula (I-C-5), Formula (I-C-6), Formula (I-C-7), and Formula (I-C-8), or a pharmaceutically acceptable salt of any of the foregoing:
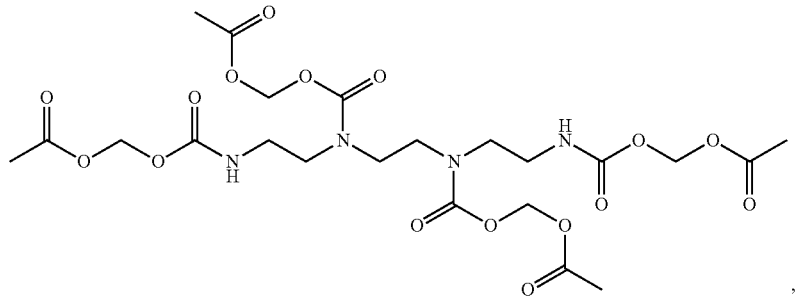
(I-C-1)
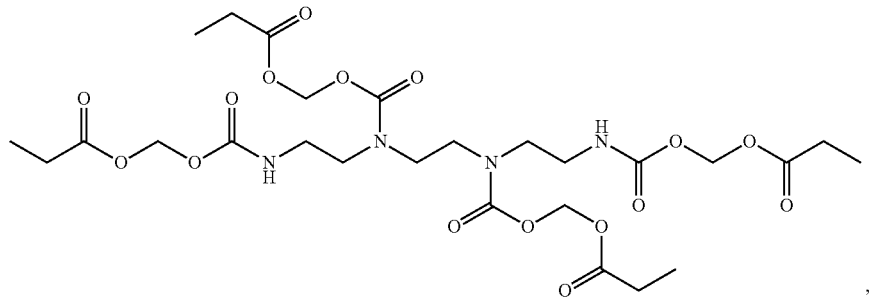
(I-C-2)
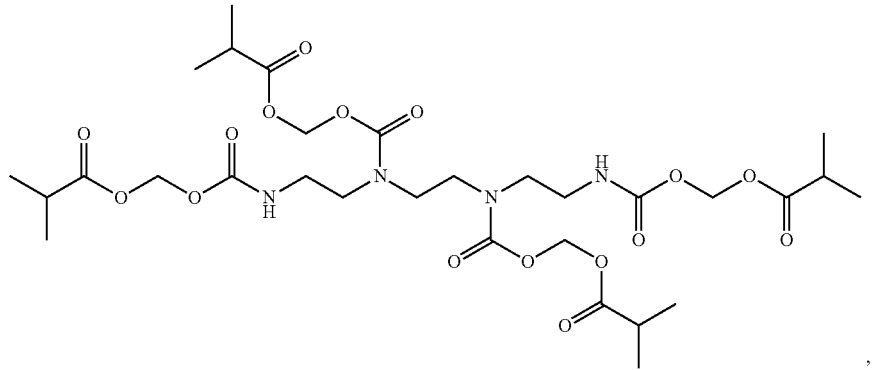
(I-C-3)
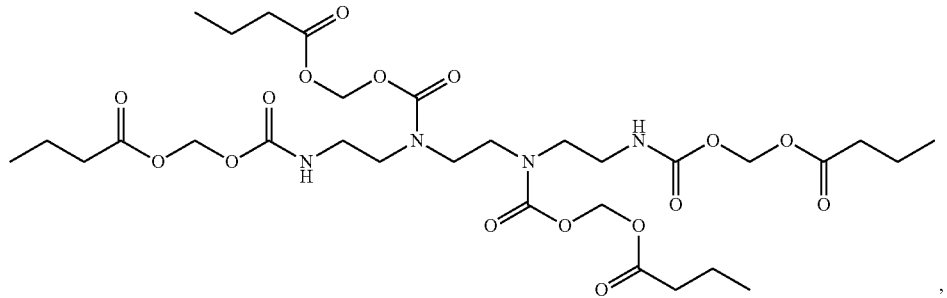
(I-C-4)

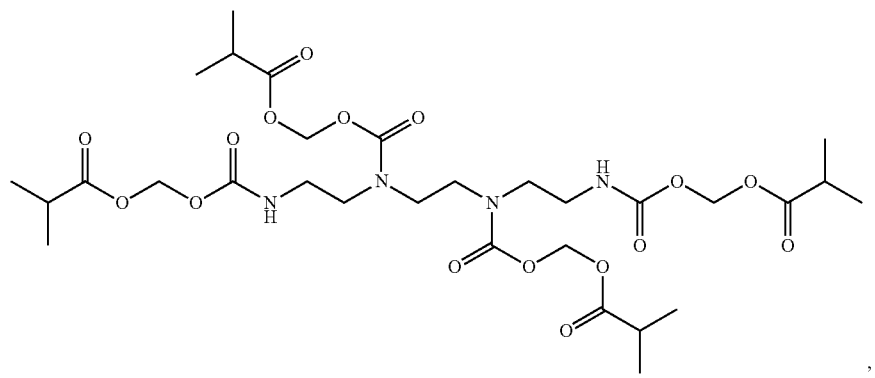
(I-C-5)

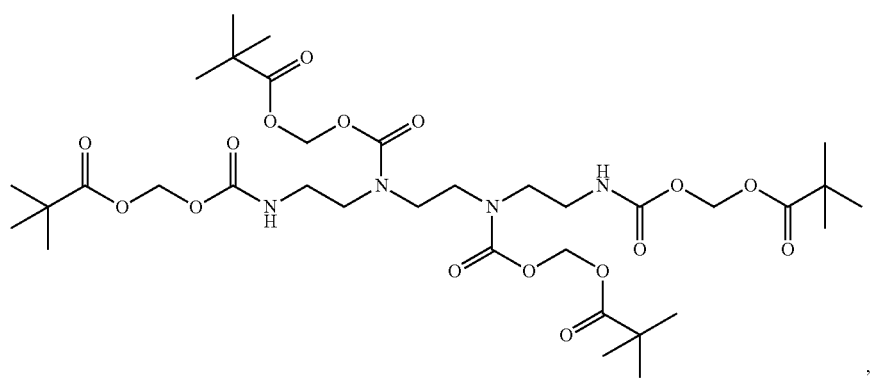
(I-C-6)

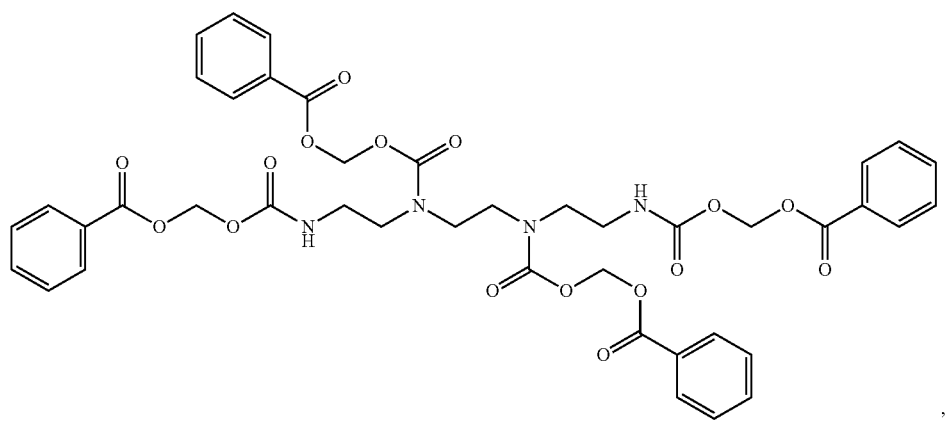
(I-C-7)

, and

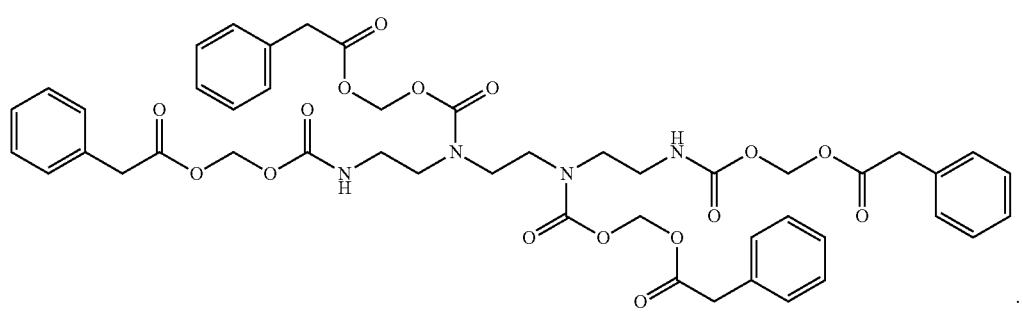
(I-C-8)

In certain embodiments of a compound of Formula (I), $W^1$ and $W^3$ are the substituent of Formula (I-a); one $W^2$ is the substituent of Formula (I-a); and the other $W^2$ is hydrogen; wherein $R^1$ is methyl, $R^2$ and $R^3$ are hydrogen, and $Y^1$ is a bond.

In certain embodiments of a compound of Formula (I), $W^1$ and $W^3$ are the substituent of Formula (I-a); one $W^2$ is the substituent of Formula (I-a); and the other $W^2$ is hydrogen; wherein $R^1$ is ethyl, $R^2$ and $R^3$ are hydrogen, and $Y^1$ is a bond.

In certain embodiments of a compound of Formula (I), $W^1$ and $W^3$ are the substituent of Formula (I-a); one $W^2$ is the substituent of Formula (I-a); and the other $W^2$ is hydrogen; wherein $R^1$ is n-propyl, $R^2$ and $R^3$ are hydrogen, and $Y^1$ is a bond.

In certain embodiments of a compound of Formula (I), $W^1$ and $W^3$ are the substituent of Formula (I-a); one $W^2$ is the substituent of Formula (I-a); and the other $W^2$ is hydrogen; wherein $R^1$ is isopropyl, $R^2$ and $R^3$ are hydrogen, and $Y^1$ is a bond.

In certain embodiments of a compound of Formula (I), $W^1$ and $W^3$ are the substituent of Formula (I-a); one $W^2$ is the substituent of Formula (I-a); and the other $W^2$ is hydrogen; wherein $R^1$ is tert-butyl, $R^2$ and $R^3$ are hydrogen, and $Y^1$ is a bond.

In certain embodiments of a compound of Formula (I), $W^1$ and $W^3$ are the substituent of Formula (I-a); one $W^2$ is the substituent of Formula (I-a); and the other $W^2$ is hydrogen; wherein $R^1$ is cyclohexyl, $R^2$ and $R^3$ are hydrogen, and $Y^1$ is a bond.

In certain embodiments of a compound of Formula (I), $W^1$ and $W^3$ are the substituent of Formula (I-a); one $W^2$ is the substituent of Formula (I-a); and the other $W^2$ is hydrogen; wherein $R^1$ is phenyl, $R^2$ and $R^3$ are hydrogen, and $Y^1$ is a bond.

In certain embodiments of a compound of Formula (I), $W^1$ and $W^3$ are the substituent of Formula (I-a); one $W^2$ is the substituent of Formula (I-a); and the other $W^2$ is hydrogen; wherein $R^1$ is benzyl, $R^2$ and $R^3$ are hydrogen, and $Y^1$ is a bond.

In certain embodiments of a compound of Formula (I), the compound is chosen from a compound of Formula (I-D-1), Formula (I-D-2), Formula (I-D-3), Formula (I-D-4), Formula (I-D-5), Formula (I-D-6), Formula (I-D-7), and Formula (I-D-8), or a pharmaceutically acceptable salt of any of the foregoing:

(I-D-1)

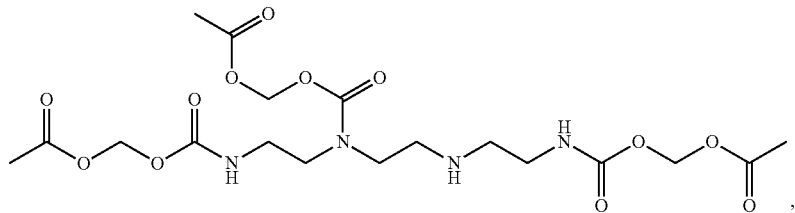

(I-D-2)

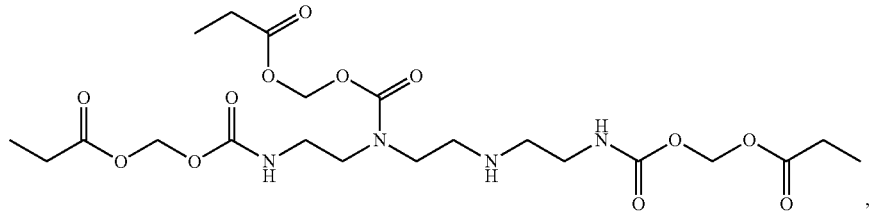

(I-D-3)

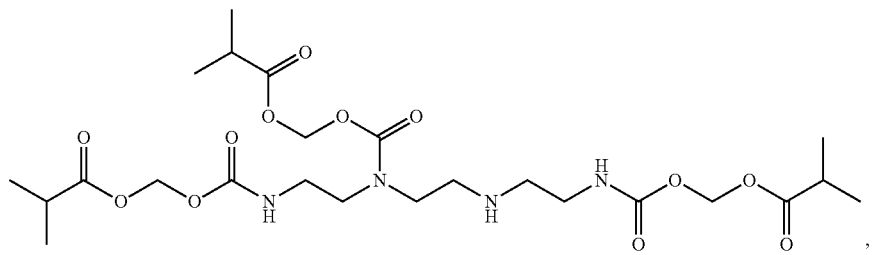

(I-D-4)

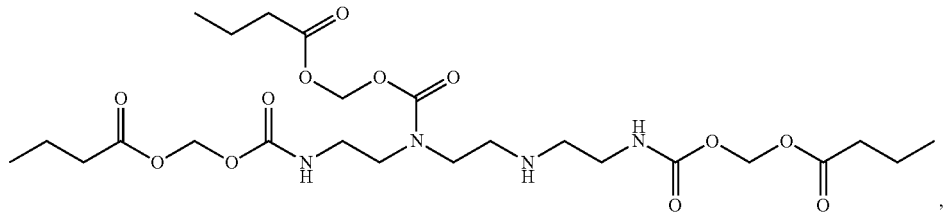

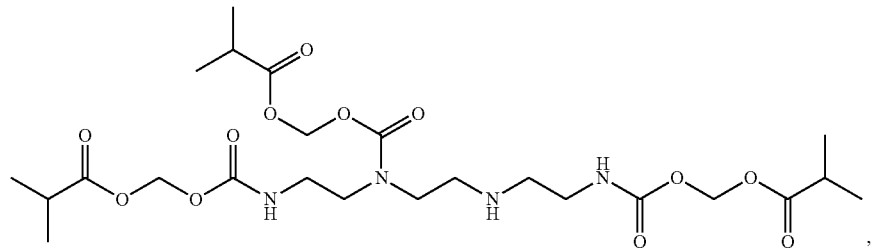

(I-D-5)

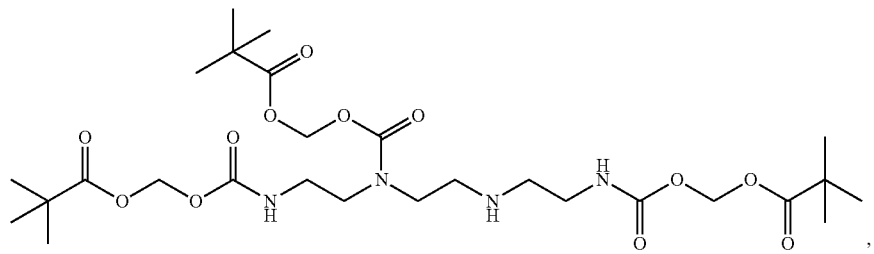

(I-D-6)

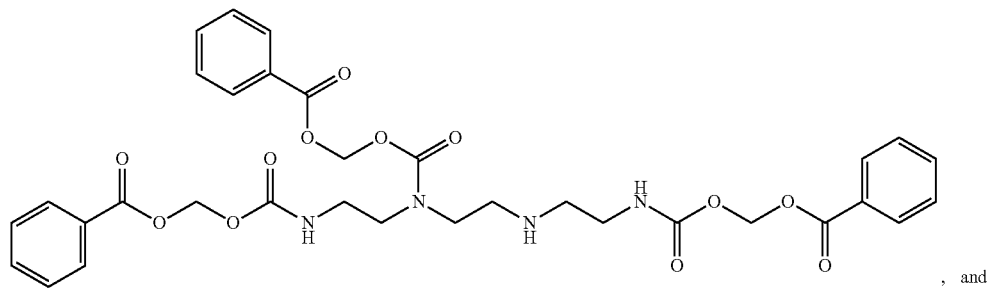

, and (I-D-7)

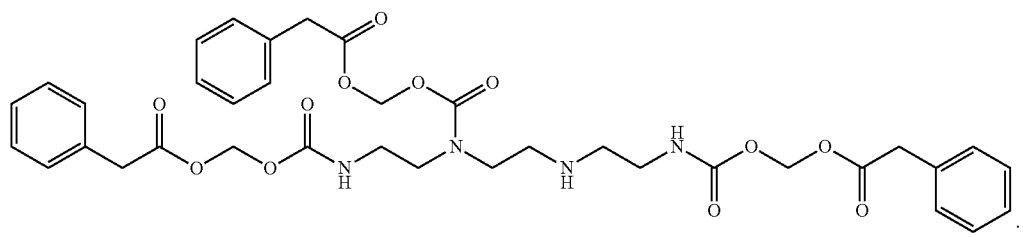

(I-D-8)

In certain embodiments of a compound of Formula (I), each $W^1$ and $W^2$ is the substituent of Formula (I-a); and $W^3$ is hydrogen; wherein $R^1$ is methyl, $R^2$ and $R^3$ are hydrogen, and $Y^1$ is a bond.

In certain embodiments of a compound of Formula (I), each $W^1$ and $W^2$ is the substituent of Formula (I-a); and $W^3$ is hydrogen; wherein $R^1$ is ethyl, $R^2$ and $R^3$ are hydrogen, and $Y^1$ is a bond.

In certain embodiments of a compound of Formula (I), each $W^1$ and $W^2$ is the substituent of Formula (I-a); and $W^3$ is hydrogen; wherein $R^1$ is n-propyl, $R^2$ and $R^3$ are hydrogen, and $Y^1$ is a bond.

In certain embodiments of a compound of Formula (I), each $W^1$ and $W^2$ is the substituent of Formula (I-a); and $W^3$ is hydrogen; wherein $R^1$ is isopropyl, $R^2$ and $R^3$ are hydrogen, and $Y^1$ is a bond.

In certain embodiments of a compound of Formula (I), each $W^1$ and $W^2$ is the substituent of Formula (I-a); and $W^3$ is hydrogen; wherein $R^1$ is tert-butyl, $R^2$ and $R^3$ are hydrogen, and $Y^1$ is a bond.

In certain embodiments of a compound of Formula (I), each $W^1$ and $W^2$ is the substituent of Formula (I-a); and $W^3$ is hydrogen; wherein $R^1$ is cyclohexyl, $R^2$ and $R^3$ are hydrogen, and $Y^1$ is a bond.

In certain embodiments of a compound of Formula (I), each $W^1$ and $W^2$ is the substituent of Formula (I-a); and $W^3$ is hydrogen; wherein $R^1$ is phenyl, $R^2$ and $R^3$ are hydrogen, and $Y^1$ is a bond.

In certain embodiments of a compound of Formula (I), each $W^1$ and $W^2$ is the substituent of Formula (I-a); and $W^3$ is hydrogen; wherein $R^1$ is benzyl, $R^2$ and $R^3$ are hydrogen, and $Y^1$ is a bond.

In certain embodiments of a compound of Formula (I), the compound is chosen from a compound of Formula (I-E-1), Formula (I-E-2), Formula (I-E-3), Formula (I-E-4), Formula (I-E-5), Formula (I-E-6), Formula (I-E-7), and Formula (I-E-8), or a pharmaceutically acceptable salt of any of the foregoing:

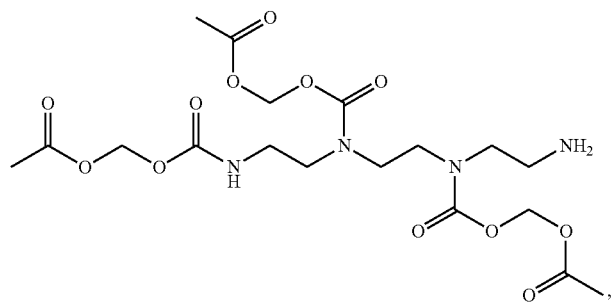
(I-E-1)
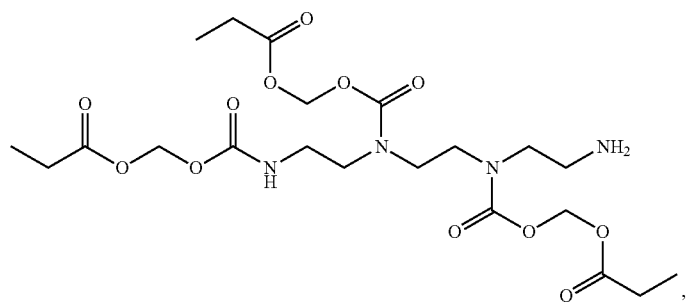
(I-E-2)
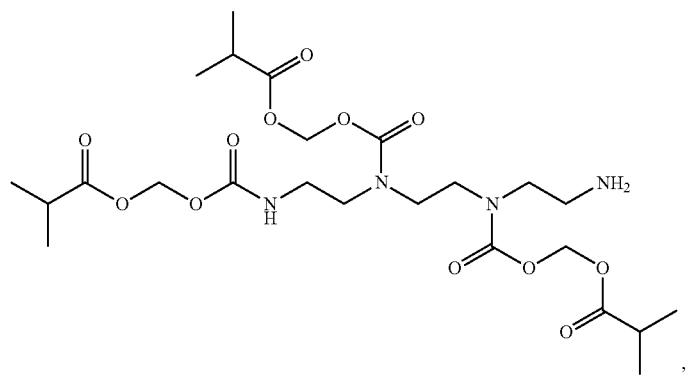
(I-E-3)
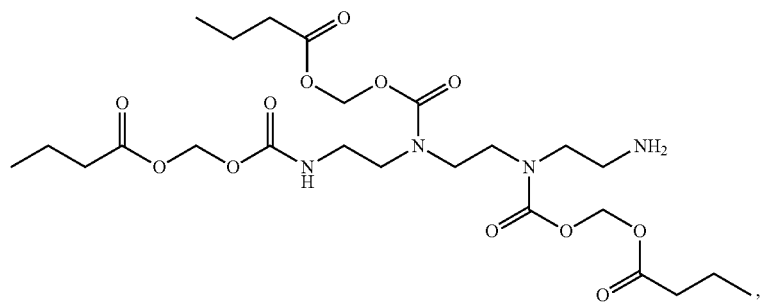
(I-E-4)

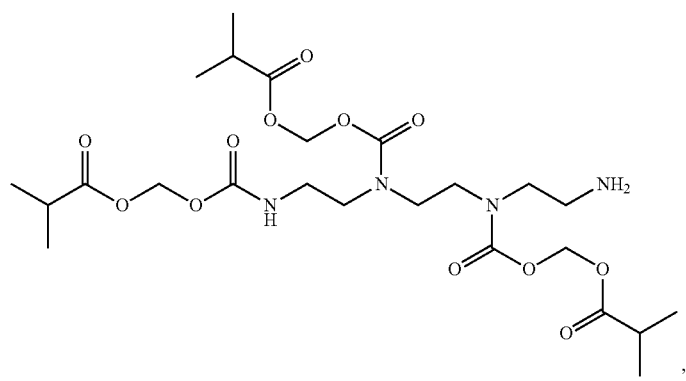
(I-E-5)
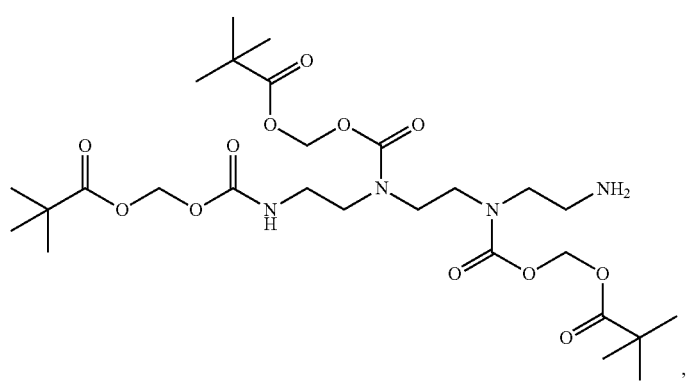
(I-E-6)
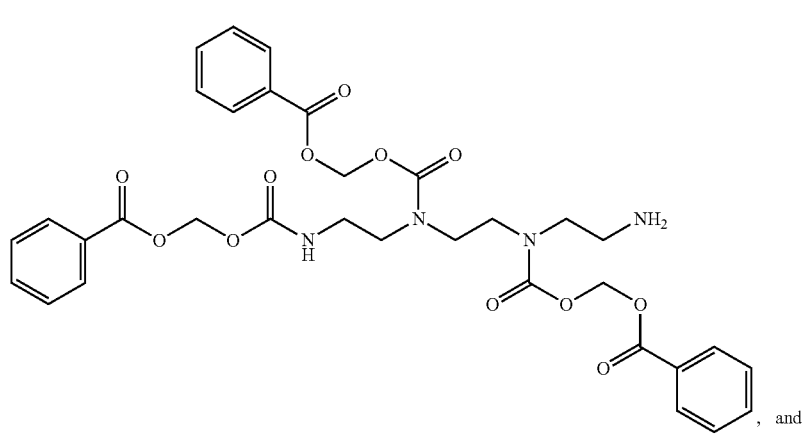
, and
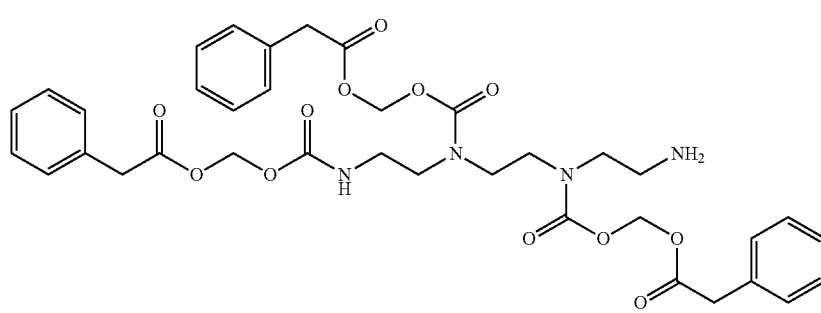
(I-E-8)
In certain embodiments of a compound of Formula (I), $W^1$ and $W^3$ are the substituent of Formula (I-b); and each $W^2$ is hydrogen; wherein $R^4$ is methyl.
In certain embodiments of a compound of Formula (I), $W^1$ and $W^3$ are the substituent of Formula (I-b); and each $W^2$ is hydrogen; wherein $R^4$ is phenyl.

In certain embodiments of a compound of Formula (I), $W^1$ is the substituent of Formula (I-b); and each $W^2$ and $W^3$ is hydrogen; wherein $R^4$ is methyl.

In certain embodiments of a compound of Formula (I), $W^1$ is the substituent of Formula (I-b); and each $W^2$ and $W^3$ is hydrogen; wherein $R^4$ is phenyl.

In certain embodiments of a compound of Formula (I), each $W^1$, $W^2$, and $W^3$ is the substituent of Formula (I-b); wherein $R^4$ is methyl.

In certain embodiments of a compound of Formula (I), each $W^1$ and $W^3$ is the substituent of Formula (I-b); one $W^2$ is a compound of Formula (I-b); and the other $W^2$ is hydrogen; wherein $R^4$ is methyl.

In certain embodiments of a compound of Formula (I), each $W^1$ and $W^2$ is the substituent of Formula (I-b); and $W^3$ is hydrogen; wherein $R^4$ is methyl.

In certain embodiments of a compound of Formula (I), the compound is chosen from a compound of Formula (I-F-1), Formula (I-F-2), Formula (I-F-3), Formula (I-F-4), Formula (I-F-5), Formula (I-F-6), and Formula (I-F-7), or a pharmaceutically acceptable salt of any of the foregoing:

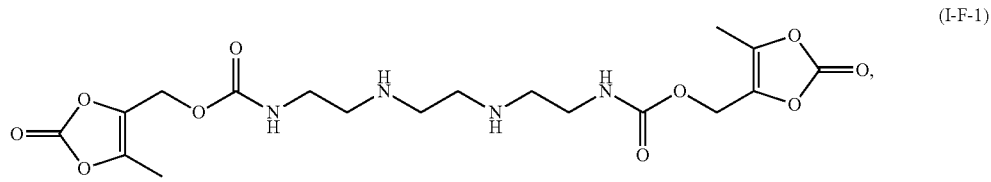

(I-F-1)

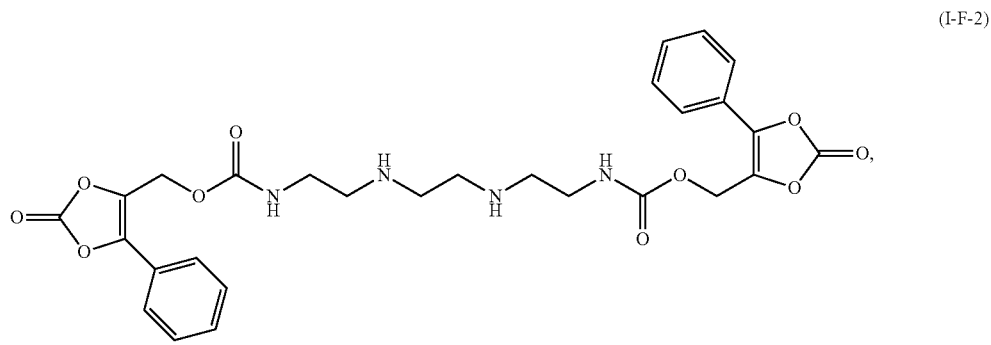

(I-F-2)

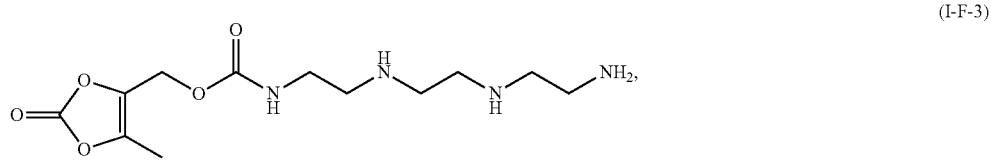

(I-F-3)

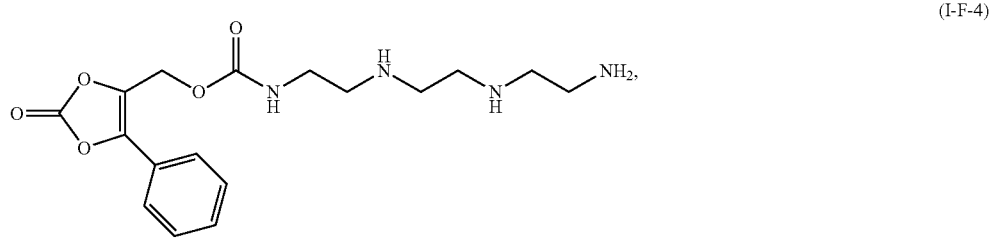

(I-F-4)

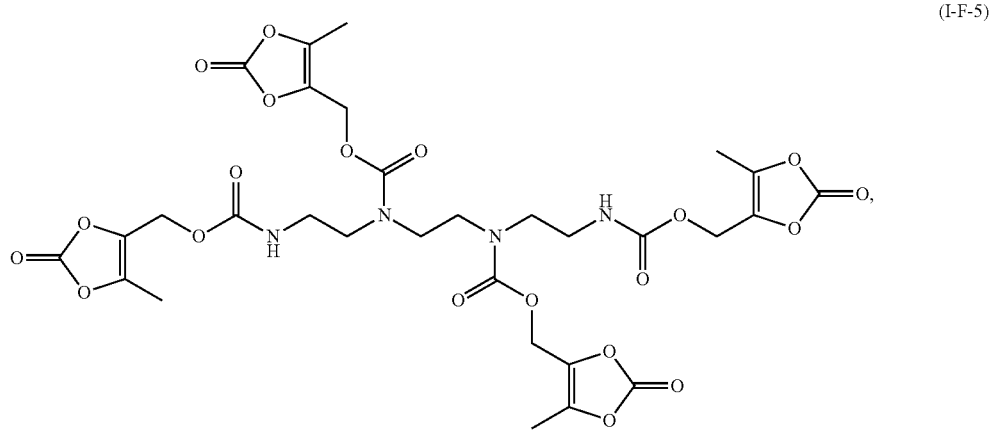

(I-F-5)

(I-F-6)

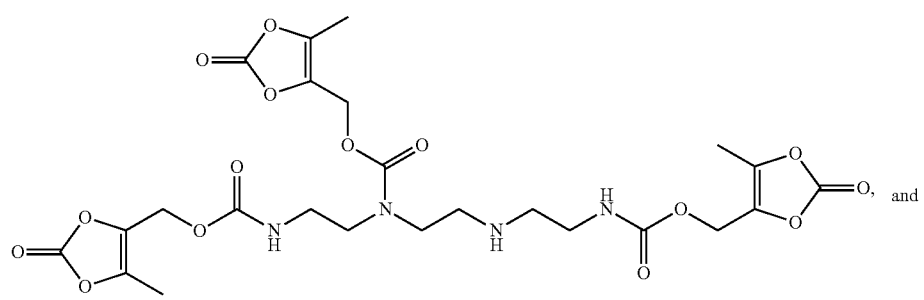

(I-F-7)

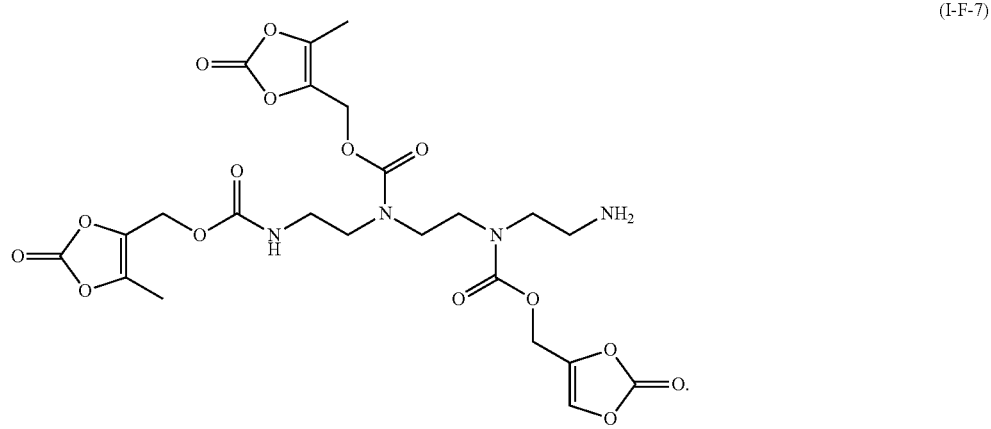

Synthesis

Compounds disclosed herein may be obtained via the synthetic methods illustrated in Schemes I-A to I-G. General synthetic methods useful in the synthesis of compounds described herein are available in the art. Starting materials useful for preparing compounds and intermediates thereof and/or practicing methods described herein are commercially available or can be prepared by well-known synthetic methods. The methods presented in the schemes provided by the present disclosure are illustrative rather than comprehensive. It will be apparent to those skilled in the art that many modifications, both to materials and methods, may be practiced without departing from the scope of the disclosure.

Compounds of Formula (I) can be prepared according to Schemes I-A to I-G:

Scheme I-A

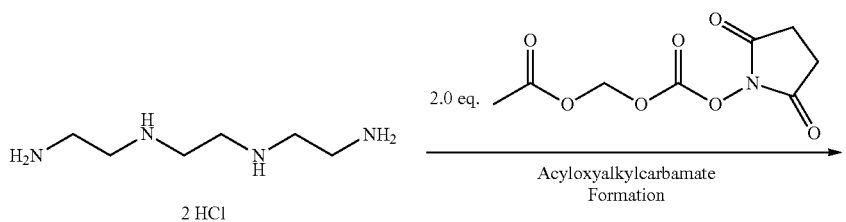

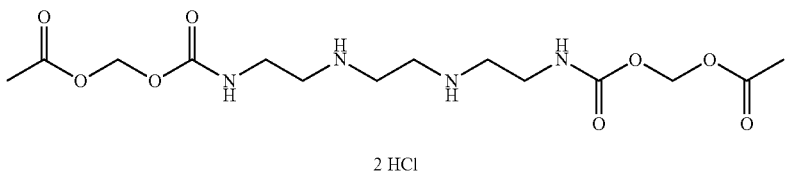

Scheme I-B
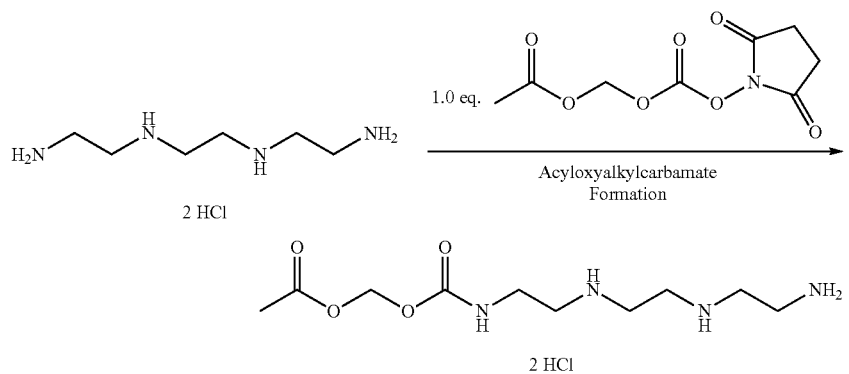
Scheme I-C
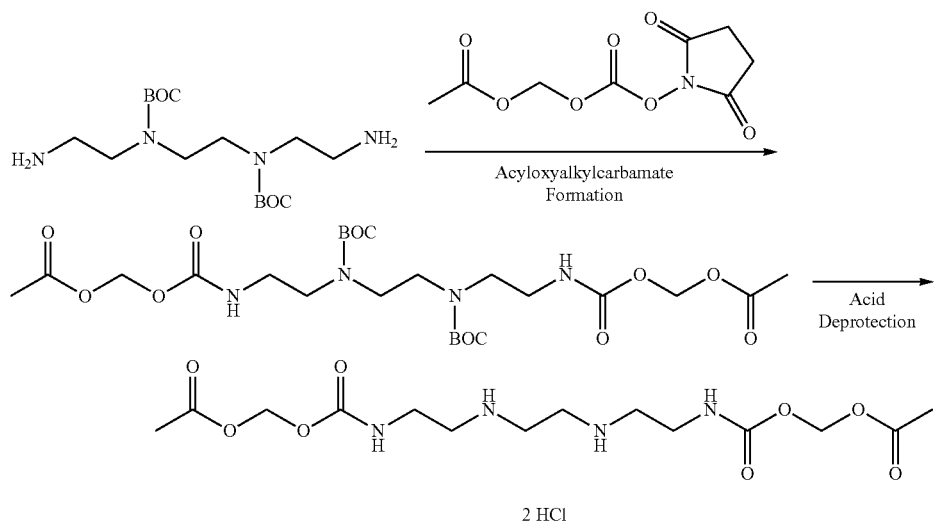
Scheme I-D
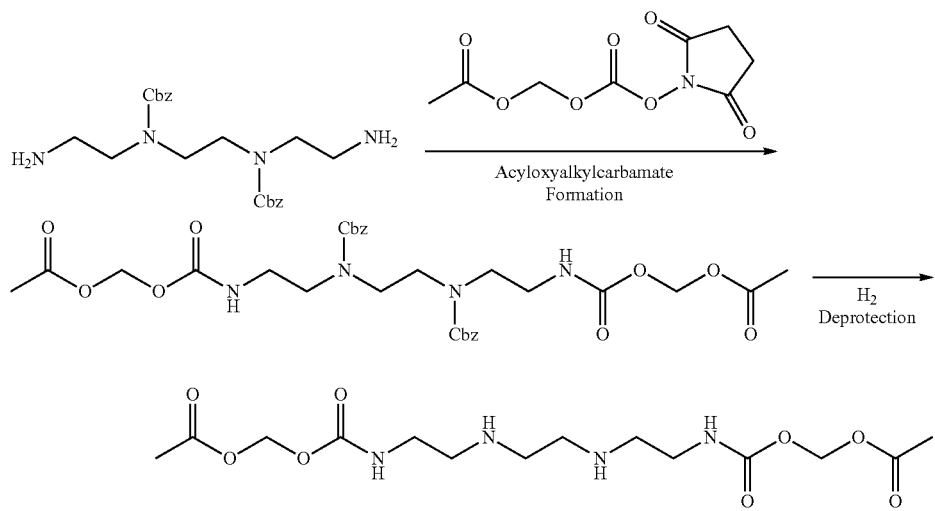

Scheme I-E
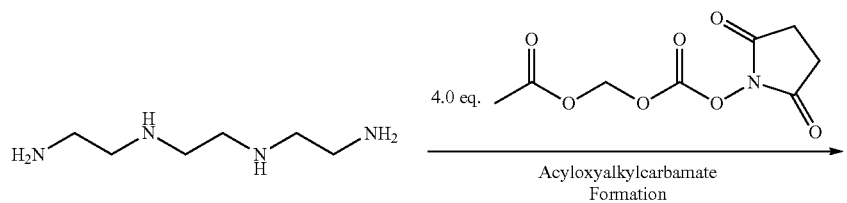
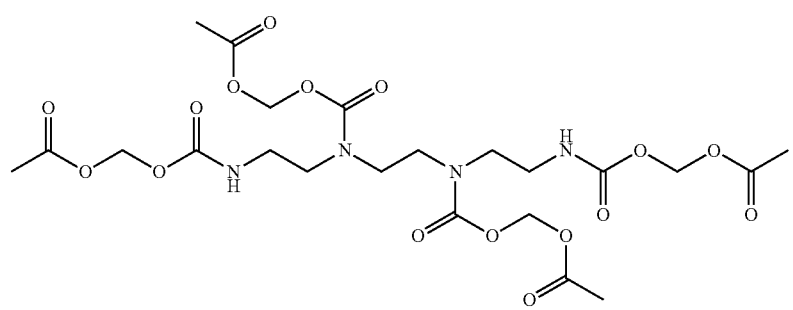
Scheme I-F
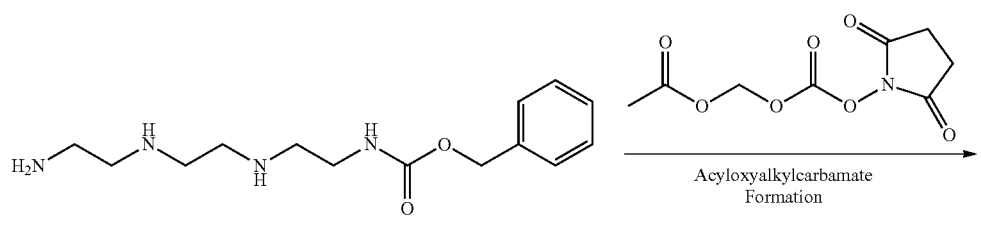
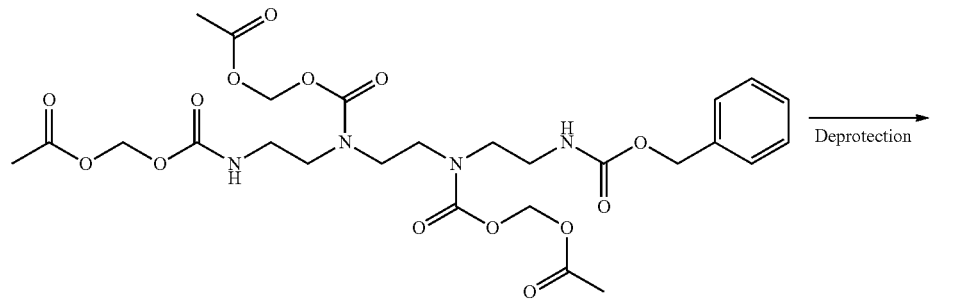
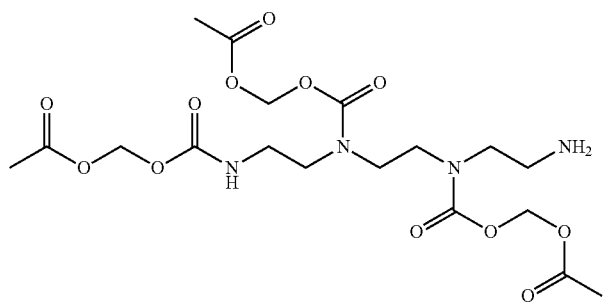

Scheme I-G

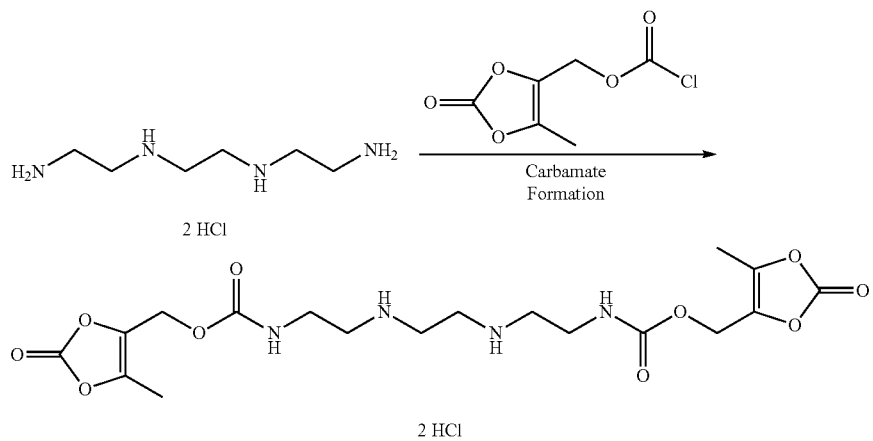

Pharmaceutical Compositions

Pharmaceutical compositions provided by the present disclosure may comprise a therapeutically effective amount of a compound of Formula (I) together with a suitable amount of one or more pharmaceutically acceptable vehicles so as to provide a composition for proper administration to a patient. Suitable pharmaceutical vehicles are described in the art.

In certain embodiments, a compound of Formula (I) may be incorporated into pharmaceutical compositions to be administered orally. Oral administration of such pharmaceutical compositions may result in uptake of a compound of Formula (I) throughout the intestine and entry into the systemic circulation. Such oral compositions may be prepared in a manner known in the pharmaceutical art and comprise a compound of Formula (I) and at least one pharmaceutically acceptable vehicle. Oral pharmaceutical compositions may include a therapeutically effective amount of a compound of Formula (I) and a suitable amount of a pharmaceutically acceptable vehicle, so as to provide an appropriate form for administration to a patient.

Compounds of Formula (I) may be incorporated into pharmaceutical compositions to be administered by any other appropriate route of administration including intradermal, intramuscular, intraperitoneal, intravenous, subcutaneous, intranasal, epidural, oral, sublingual, intracerebral, intravaginal, transdermal, rectal, inhalation, or topical.

Pharmaceutical compositions comprising a compound of Formula (I) and may be manufactured by means of conventional mixing, dissolving, granulating, dragee-making, levigating, emulsifying, encapsulating, entrapping, or lyophilizing processes. Pharmaceutical compositions may be formulated in a conventional manner using one or more physiologically acceptable carriers, diluents, excipients, or auxiliaries, which facilitate processing of compounds of Formula (I) or crystalline forms thereof and one or more pharmaceutically acceptable vehicles into formulations that can be used pharmaceutically. Proper formulation is dependent upon the route of administration chosen. Pharmaceutical compositions provided by the present disclosure may take the form of solutions, suspensions, emulsion, tablets, pills, pellets, capsules, capsules containing liquids, powders, sustained-release formulations, suppositories, emulsions, aerosols, sprays, suspensions, or any other form suitable for administration to a patient.

Pharmaceutical compositions provided by the present disclosure may be formulated in a unit dosage form. A unit dosage form refers to a physically discrete unit suitable as a unitary dose for patients undergoing treatment, with each unit containing a predetermined quantity of a compound of Formula (I) calculated to produce an intended therapeutic effect. A unit dosage form may be for a single daily dose, for administration 2 times per day, or one of multiple daily doses, e.g., 3 or more times per day. When multiple daily doses are used, a unit dosage form may be the same or different for each dose. One or more dosage forms may comprise a dose, which may be administered to a patient at a single point in time or during a time interval.

Pharmaceutical compositions comprising a compound of Formula (I) may be formulated for immediate release.

In certain embodiments, an oral dosage form provided by the present disclosure may be a controlled release dosage form. Controlled delivery technologies can improve the absorption of a drug in a particular region or regions of the gastrointestinal tract. Controlled drug delivery systems may be designed to deliver a drug in such a way that the drug level is maintained within a therapeutically effective window and effective and safe blood levels are maintained for a period as long as the system continues to deliver the drug with a particular release profile in the gastrointestinal tract. Controlled drug delivery may produce substantially constant blood levels of a drug over a period of time as compared to fluctuations observed with immediate release dosage forms. For some drugs, maintaining a constant blood and tissue concentration throughout the course of therapy is the most desirable mode of treatment. Immediate release of drugs may cause blood levels to peak above the level required to elicit a desired response, which may waste the drug and may cause or exacerbate toxic side effects. Controlled drug delivery can result in optimum therapy, and not only can reduce the frequency of dosing, but may also reduce the severity of side effects. Examples of controlled release dosage forms include dissolution controlled systems, diffusion controlled systems, ion exchange resins, osmotically controlled systems, erodable matrix systems, pH independent formulations, gastric retention systems, and the like.

An appropriate oral dosage form for a particular pharmaceutical composition provided by the present disclosure may depend, at least in part, on the gastrointestinal absorption properties of a compound of Formula (I) the stability of a compound of Formula (I) in the gastrointestinal tract, the pharmacokinetics of a compound of Formula (I) and the intended therapeutic profile. An appropriate controlled release oral dosage form may be selected for a particular compound of Formula (I). For example, gastric retention oral dosage forms may be appropriate for compounds absorbed primarily from the upper gastrointestinal tract, and sustained release oral dosage forms may be appropriate for compounds absorbed primarily from the lower gastrointestinal tract. Certain compounds are absorbed primarily from the small intestine. In general, compounds traverse the length of the small intestine in about 3 to 5 hours. For compounds that are not easily absorbed by the small intestine or that do not dissolve readily, the window for active agent absorption in the small intestine may be too short to provide a desired therapeutic effect.

In certain embodiments, pharmaceutical compositions provided by the present disclosure may be practiced with dosage forms adapted to provide sustained release of a compound of Formula (I) upon oral administration. Sustained release oral dosage forms may be used to release drugs over a prolonged time period and are useful when it is desired that a drug or drug form be delivered to the lower gastrointestinal tract. Sustained release oral dosage forms include any oral dosage form that maintains therapeutic concentrations of a drug in a biological fluid such as the plasma, blood, cerebrospinal fluid, or in a tissue or organ for a prolonged time period. Sustained release oral dosage forms include diffusion-controlled systems such as reservoir devices and matrix devices, dissolution-controlled systems, osmotic systems, and erosion-controlled systems. Sustained release oral dosage forms and methods of preparing the same are well known in the art.

An appropriate dose of a compound of Formula (I) or pharmaceutical composition comprising a compound of Formula (I) may be determined according to any one of several well-established protocols. For example, animal studies such as studies using mice, rats, dogs, and/or monkeys may be used to determine an appropriate dose of a pharmaceutical compound. Results from animal studies may be extrapolated to determine doses for use in other species, such as for example, humans.

Uses

Compounds of Formula (I) and pharmaceutical compositions thereof may be administered to a patient suffering from any disease including a disorder, condition, or symptom for which trientine is known or hereafter discovered to be therapeutically effective. Indication for which trientine has been prescribed, and hence for which a compound of Formula (I), or pharmaceutical compositions thereof is also expected to be effective, includes Wilson's disease.

Methods of treating a disease in a patient provided by the present disclosure comprise administering to a patient in need of such treatment a therapeutically effective amount of a compound of Formula (I). Compounds of Formula (I) or pharmaceutical compositions thereof may provide therapeutic or prophylactic plasma and/or blood concentrations of trientine following administration to a patient.

Compounds of Formula (I) may be included in a pharmaceutical composition and/or dosage form adapted for oral administration, although compound of Formula (I) may also be administered by any other appropriate route, such as for example, by injection, infusion, inhalation, transdermal, or absorption through epithelial or mucosal membranes (e.g., oral, rectal, and/or intestinal mucosa).

Compounds of Formula (I) may be administered in an amount and using a dosing schedule as appropriate for treatment of a particular disease. Daily doses of a compound of Formula (I) may range from about 0.01 mg/kg to about 50 mg/kg, from about 0.1 mg/kg to about 20 mg/kg, from about 1 mg/kg to about 25 mg/kg, and in certain embodiments, from about 5 mg/kg to about 25 mg/kg. In certain embodiments, compounds of Formula (I) may be administered at a dose over time from about 1 mg to about 10 g per day, from about 250 mg to about 5 g per day, from about 500 mg to about 5 g per day, from about 750 mg to about 2.5 g per day, and in certain embodiments from about 750 mg to about 1.0 g per day. An appropriate dose of a compound of Formula (I) may be determined based on several factors, including, for example, the body weight and/or condition of the patient being treated, the severity of the disease being treated, the incidence and/or severity of side effects, the manner of administration, and the judgment of the prescribing physician. Appropriate dose ranges may be determined by methods known to those skilled in the art.

Compounds of Formula (I) may be assayed in vitro and in vivo for the desired therapeutic or prophylactic activity prior to use in humans. In vivo assays, for example using appropriate animal models, may also be used to determine whether administration of a compound of Formula (I) is therapeutically effective.

In certain embodiments, a therapeutically effective dose of a compound of Formula (I) may provide therapeutic benefit without causing substantial toxicity including adverse side effects. Toxicity of compounds of Formula (I) and/or metabolites thereof may be determined using standard pharmaceutical procedures and may be ascertained by those skilled in the art. The dose ratio between toxic and therapeutic effect is the therapeutic index. A dose of a compound of Formula (I) may be within a range capable of establishing and maintaining a therapeutically effective circulating plasma and/or blood concentration of a compound of Formula (I) that exhibits little or no toxicity Trientine prodrug of Formula (I) may be used to treat diseases, disorders, conditions, and symptoms of any of the foregoing for which trientine is known to provide or is later found to provide therapeutic benefit. Trientine is known to be effective in treating Wilson's disease. Hence, compounds of Formula (I) may be used to treat the foregoing disease and disorder. The underlying etiology of any of the foregoing diseases being treated may have a multiplicity of origins. Further, in certain embodiments, a therapeutically effective amount of one or more compounds of Formula (I) may be administered to a patient, such as a human, as a preventative measure against various diseases or disorders.

Administration

Compounds of Formula (I) and pharmaceutical compositions thereof may be administered orally or by any other appropriate route, for example, by infusion or bolus injection, by absorption through epithelial or mucocutaneous linings (e.g., oral mucosa, rectal, and intestinal mucosa, etc.). Other suitable routes of administration include, but are not limited to, intradermal, intramuscular, intraperitoneal, intravenous, subcutaneous, intranasal, epidural, oral, sublingual, intracerebral, intravaginal, transdermal, rectal, inhalation, or topical.

Administration may be systemic or local. Various delivery systems are known, e.g., encapsulation in liposomes, microparticles, microcapsules, capsules, etc.) that may be used to administer a compound and/or pharmaceutical composition.

The amount of a compound of Formula (I) that will be effective in the treatment of a disease in a patient will depend, in part, on the nature of the condition and can be determined by standard clinical techniques known in the art. In addition, in vitro or in vivo assays may be employed to help identify optimal dosage ranges. A therapeutically effective amount of a compound of Formula (I) to be administered may also depend on, among other factors, the subject being treated, the weight of the subject, the severity of the disease, the manner of administration, and the judgment of the prescribing physician.

For systemic administration, a therapeutically effective dose may be estimated initially from in vitro assays. For example, a dose may be formulated in animal models to achieve a beneficial circulating composition concentration range. Initial doses may also be estimated from in vivo data, e.g., animal models, using techniques that are known in the art. Such information may be used to more accurately determine useful doses in humans. One having ordinary skill in the art may optimize administration to humans based on animal data.

A dose may be administered in a single dosage form or in multiple dosage forms. When multiple dosage forms are used the amount of compound contained within each dosage form may be the same or different. The amount of a compound of Formula (I) contained in a dose may depend on the route of administration and whether the disease in a patient is effectively treated by acute, chronic, or a combination of acute and chronic administration.

In certain embodiments an administered dose is less than a toxic dose. Toxicity of the compositions described herein may be determined by standard pharmaceutical procedures in cell cultures or experimental animals, e.g., by determining the LD50 (the dose lethal to 50% of the population) or the LD100 (the dose lethal to 100% of the population). The dose ratio between toxic and therapeutic effect is the therapeutic index. In certain embodiments, a trientine prodrug may exhibit a high therapeutic index. The data obtained from these cell culture assays and animal studies may be used in formulating a dosage range that is not toxic for use in humans. A dose of a trientine prodrug provided by the present disclosure may be within a range of circulating concentrations in for example the blood, plasma, or central nervous system, that include the effective dose and that exhibits little or no toxicity. A dose may vary within this range depending upon the dosage form employed and the route of administration utilized. In certain embodiments, an escalating dose may be administered.

Combination Therapy

Methods provided by the present disclosure further comprise administering one or more pharmaceutically active compounds in addition to a compound of Formula (I). Such compounds may be provided to treat the same disease or a different disease than the disease being treated with the trientine prodrug of Formula (I).

In certain embodiments, a compound of Formula (I) may be used in combination with at least one other therapeutic agent. In certain embodiments, a compound of Formula (I) may be administered to a patient together with another compound for treating diseases and conditions involving hereditary, immunological, autoimmune, and/or inflammatory processes including: Wilson's disease; psoriasis; asthma, chronic obstructive pulmonary diseases, and arthritis; cardiac insufficiency including left ventricular insufficiency, myocardial infarction and angina pectoris; mitochondrial and neurodegenerative diseases such as Parkinson's disease, Alzheimer's disease, Huntington's disease, retinopathia pigmentosa and mitochondrial encephalomyopathy; transplantation rejection; autoimmune diseases including multiple sclerosis (MS); ischemia and reperfusion injury (AGE-induced genome damage; and others. In certain embodiments, a compound of Formula (I) may be administered to a patient together with another compound for treating psoriasis, multiple sclerosis, an inflammatory bowel disease, asthma, chronic obstructive pulmonary disease, and arthritis.

A compound of Formula (I) and the at least one other therapeutic agent may act additively or, and in certain embodiments, synergistically. The at least one additional therapeutic agent may be included in the same dosage form as a compound of Formula (I) or may be provided in a separate dosage form. Methods provided by the present disclosure can further include, in addition to administering a compound of Formula (I), administering one or more therapeutic agents effective for treating the same or different disease than the disease being treated by a compound of Formula (I). Methods provided by the present disclosure include administration of a compound of Formula (I) and one or more other therapeutic agents provided that the combined administration does not inhibit the therapeutic efficacy of the trientine prodrug and/or does not typically produce significant and/or substantial adverse combination effects.

In certain embodiments, dosage forms comprising a compound of Formula (I) may be administered concurrently with the administration of another therapeutic agent, which may be part of the same dosage form as, or in a different dosage form than that comprising a compound of Formula (I). A compound of Formula (I) may be administered prior or subsequent to administration of another therapeutic agent. In certain embodiments of combination therapy, the combination therapy may comprise alternating between administering a compound of Formula (I) and a composition comprising another therapeutic agent, e.g., to minimize adverse drug effects associated with a particular drug. When a compound of Formula (I) is administered concurrently with another therapeutic agent that potentially may produce an adverse drug effect including, but not limited to, toxicity, the other therapeutic agent may advantageously be administered at a dose that falls below the threshold at which the adverse drug reaction is elicited.

In certain embodiments, dosage forms comprising a compound of Formula (I) may be administered with one or more substances to enhance, modulate and/or control release, bioavailability, therapeutic efficacy, therapeutic potency, stability, and the like of a trientine prodrug of Formula (I). For example, to enhance the therapeutic efficacy of a compound of Formula (I), the trientine prodrug may be co-administered with one or more active agents to increase the absorption or diffusion of the compound of Formula (I) from the gastrointestinal tract to the systemic circulation, or to inhibit degradation of the compound of Formula (I) in the blood of a patient. In certain embodiments, a compound of Formula (I) may be co-administered with an active agent having pharmacological effects that enhance the therapeutic efficacy of a compound of Formula (I).

In certain embodiments, a compound of Formula (I) or a pharmaceutical composition thereof may be administered to a patient for treating Wilson's disease in combination with a therapy or another therapeutic agent known or believed to be effective in treating Wilson's disease. Drugs useful for treating Wilson's disease include D-penicillamine and tiopronin.

EXAMPLES

The following examples describe in detail the synthesis of compounds of Formula (I). It will be apparent to those skilled in the art that many modifications, both to materials and methods, may be practiced without departing from the scope of the disclosure.

General Experimental Protocols

All reagents and solvents that can be purchased from commercial suppliers may be used without further purification or manipulation. Non-commercially available reagents may be synthesized from commercially available starting materials, and by adapting methods well known in the art.

Analytical LC/MS was performed on a Agilent 1100 equipped with AB Sciex API 2000 or a Waters 2790 equipped with a Waters Micromass QZ mass spectrometer and a Phenomenex Luna C-18 analytical column. Preparative HPLC purification was performed on a Agilent 1100. Both analytical and preparative HPLC used acetonitrile/water gradients containing 0.05% formic acid. Normal-phase silica gel purification was performed on a ISCO CombiFlash Companion purification system using either a mixture of methanol and dichloromethane or ethyl acetate and hexanes. Chemical names were generated with Accelrys Draw 4.1 SP1, version MDL.Draw.Editor 4.1. 100.70 (Accelrys, Inc., San Diego, Calif.).

General Synthetic Procedure

General Procedure: Acyloxyalkylcarbamate/Carbamate Formation

An amino-containing compound (1.0 equivalent) is combined with an activated ester such as (2,5-dioxopyrrolidin-1-yl)oxycarbonyloxymethyl acetate or (5-methyl-2-oxo-1,3-dioxol-4-yl)methyl carbonochloridate (1.0 to 6.0 equivalents) in 1-20 mL/1.0 mmol of an inert solvent such as dichloromethane (DCM), ethyl acetate (EtOAc), N-methylpyrrolidone (NMP), N,N-dimethylformamide (DMF), N,N-dimethylacetamide (DMA, DMAc), acetonitrile (ACN, MeCN), dimethylsulfoxide (DMSO), tetrahydrofuran (THF), toluene, water, or mixtures thereof. To the solution, an appropriate inorganic base (0.0 to 5.0 equivalents) such as $NaHCO_3$, $Na_2CO_3$, $KHCO_3$, $K_2CO_3$, $CsHCO_3$, and $Cs_2CO_3$ or an organic secondary or tertiary base such as dicyclohexylamine (DCHA), triethylamine (TEA), and diisopropylethylamine (DIEA) is added. The reaction mixture is stirred from about 1 to about 72 h at a temperature between 0° C. to 40° C. The mixture is then diluted with an appropriate organic solvent such as methyl tert-butyl ether (MTBE), diethyl ether ($Et_2O$), ethylacetate (EtOAc), dichloromethane (DCM), or mixtures thereof, washed with water and brine, and dried over anhydrous sodium sulfate ($Na_2SO_4$) or magnesium sulfate ($MgSO_4$). After filtration, the organic solvents are removed under reduced pressure using a rotary evaporator. If required, the crude reaction products are further purified by well known purification techniques such as silica gel flash column chromatography, mass-guided reversed-phase preparative HPLC/lyophilization, precipitation, or crystallization.

Example 1

2-[2-[2-(Acetoxymethoxycarbonylamino)ethylamino]ethylamino]ethylcarbamoyloxymethyl acetate (1)

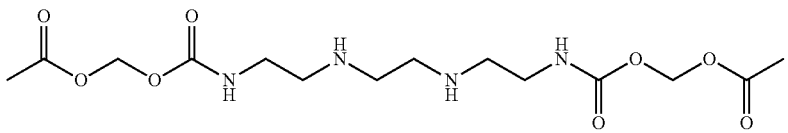 [SMILES: CC(=O)OCOC(=O)NCCNCCNCCNC(=O)OCOC(C)=O]

A mixture of trientene hydrochloride (0.20 g, 1.0 eq) and (2,5-dioxopyrrolidin-1-yl)oxycarbonyloxymethyl acetate (2.0 eq) in ACN/water (or DMF) (5 mL) was stirred at 20° C. overnight. The reaction was concentrated in vacuo to a residue and then purified by reverse-phase (C-18) liquid chromatography using water and acetonitrile as eluents to yield compound (1).

Alternatively, a mixture of tert-butyl N-(2-aminoethyl)-N-[2-[2-aminoethyl(tert-butoxycarbonyl)amino]ethyl]carbamate (0.50 g, 1.0 eq) (U.S. Pat. No. 8,394,992), (2,5-dioxopyrrolidin-1-yl)oxycarbonyloxymethyl acetate (2.0 eq), and $NaHCO_3$ (or TEA) (3.0 eq) in ACN/water (or DMF) (10 mL) was stirred at 20° C. overnight. The reaction was concentrated in vacuo to a residue and then purified by reverse-phase (C-18) liquid chromatography using water and acetonitrile as eluents to yield compound (1a).

A mixture of compound (1a) (0.10 g, 1.0 eq) and HCl in 1,4-dioxane (20 eq, 4.0 M) in 1,4-dioxane (5 mL) was stirred at 20° C. for 1 to 4 hours and then concentrated in vacuo to yield compound (1). MS (ESI): m/z 379.2 (M+H)+.

Example 2

2-[2-[2-(2-Methylpropanoyloxymethoxycarbonylamino)ethylamino]ethylamino]ethylcarbamoyloxymethyl 2-methylpropanoate (2)

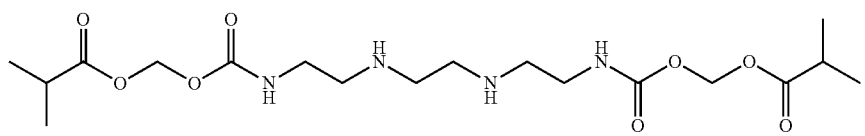 [SMILES: CC(C)C(=O)OCOC(=O)NCCNCCNCCNC(=O)OCOC(=O)C(C)C]

Compound (2) was prepared according to the method described in Example 1 and substituting (2,5-dioxopyrrolidin-1-yl)oxycarbonyloxymethyl acetate with (2,5-dioxopyrrolidin-1-yl)oxycarbonyloxymethyl 2-methylpropanoate. MS (ESI): m/z 435.2 (M+H)+.

Example 3

2-[2-[2-(2,2-Dimethylpropanoyloxymethoxycarbonylamino)ethylamino]ethylamino]ethylcarbamoyloxy methyl 2,2-dimethylpropanoate (3)

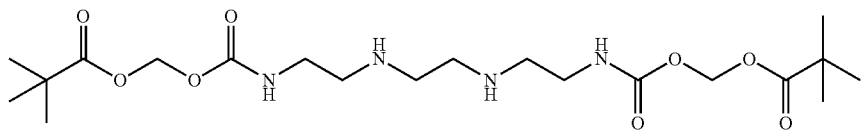 [SMILES: CC(C)(C)C(=O)OCOC(=O)NCCNCCNCCNC(=O)OCOC(=O)C(C)(C)C]

Compound (3) was prepared according to the method described in Example 1 and substituting (2,5-dioxopyrrolidin-1-yl)oxycarbonyloxymethyl acetate with (2,5-dioxopyrrolidin-1-yl)oxycarbonyloxymethyl 2,2-dimethylpropanoate. MS (ESI): m/z 463.3 (M+H)+.

Example 4

2-[2-[2-(Cyclohexanecarbonyloxymethoxycarbonylamino)ethylamino]ethylamino]ethylcarbamoyloxymethyl cyclohexanecarboxylate (4)

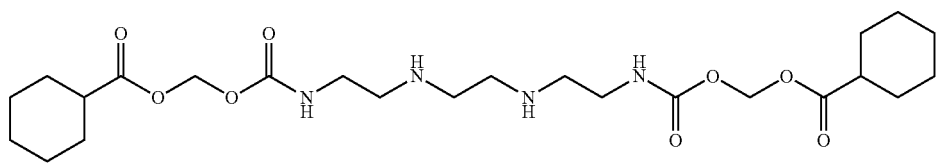 [SMILES: O=C(NCCNCCNCCNC(=O)OCOC(=O)C1CCCCC1)OCOC(=O)C1CCCCC1]

Compound (4) was prepared according to the method described in Example 1 and substituting (2,5-dioxopyrrolidin-1-yl)oxycarbonyloxymethyl acetate with (2,5-dioxopyrrolidin-1-yl)oxycarbonyloxymethyl cyclohexanecarboxylate. MS (ESI): m/z 515.3 (M+H)+.

Example 5

2-[2-[2-(Benzoyloxymethoxycarbonylamino)ethylamino]ethylamino]ethylcarbamoyloxymethyl benzoate (5)

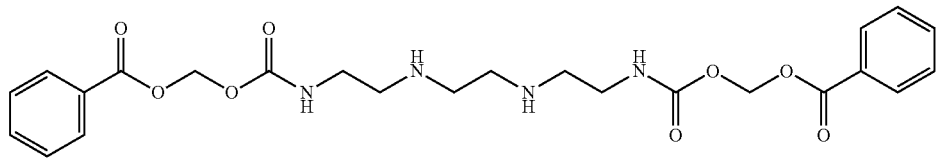 [SMILES: O=C(NCCNCCNCCNC(=O)OCOC(=O)c1ccccc1)OCOC(=O)c1ccccc1]

Compound (5) was prepared according to the method described in Example 1 and substituting (2,5-dioxopyrrolidin-1-yl)oxycarbonyloxymethyl acetate with (2,5-dioxopyrrolidin-1-yl)oxycarbonyloxymethyl benzoate. MS (ESI): m/z 503.2 (M+H)+.

Example 6

(5-Methyl-2-oxo-1,3-dioxol-4-yl)methyl N-[2-[2-[2-[(5-methyl-2-oxo-1,3-dioxol-4-yl)methoxycarbonylamino]ethylamino]ethylamino]ethyl]carbamate (6)

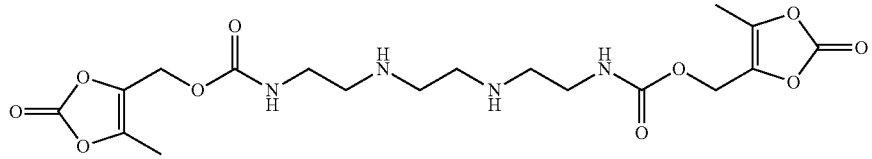 [SMILES: Cc1oc(=O)oc1COC(=O)NCCNCCNCCNC(=O)OCc1oc(=O)oc1C]

Compound (6) was prepared according to the method described in Example 1 and substituting (2,5-dioxopyrrolidin-1-yl)oxycarbonyloxymethyl acetate with (5-methyl-2-oxo-1,3-dioxol-4-yl)methyl carbonochloridate. MS (ESI): m/z 459.2 (M+H)+.

The invention claimed is:

1. A compound according to Formula (I):

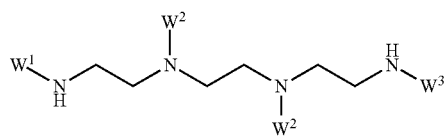

or a pharmaceutically acceptable salt thereof, wherein:
$W^1$ is chosen from substituents of Formula (I-a) and Formula (I-b); and
each $W^2$ and $W^3$ is independently chosen from hydrogen and substituents of Formula (I-a) and Formula (I-b):

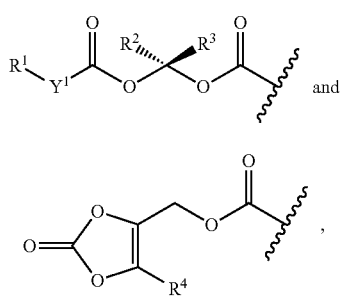

wherein
$R^1$, $R^2$, $R^3$, and $R^4$ are independently chosen from hydrogen, $C_{1-6}$ alkyl, $C_{1-6}$ heteroalkyl, $C_{3-12}$ cycloalkyl, $C_{3-12}$ heterocycloalkyl, $C_{5-10}$ aryl, and $C_{5-10}$ heteroaryl; and
$Y^1$ is chosen from a bond and —O—.

2. The compound according to claim 1, wherein $W^1$ is chosen from the substituents of Formula (I-a) and Formula (I-b), wherein $R^1$, $R^2$, $R^3$, and $R^4$ are independently chosen from hydrogen, methyl, ethyl, n-propyl, isopropyl, tert-butyl, cyclohexyl, phenyl, and benzyl; and $Y^1$ is chosen from a bond and —O—.

3. The compound according to claim 1, wherein $W^1$ is chosen from the substituent of Formula (I-a), wherein $R^1$ is chosen from methyl, ethyl, isopropyl, tert-butyl, cyclohexyl, phenyl, and benzyl; $R^2$ and $R^3$ are hydrogen; and $Y^1$ is a bond.

4. The compound according to claim 1, wherein $W^1$ is chosen from the substituent of Formula (I-b), wherein $R^4$ is chosen from methyl, ethyl, isopropyl, tert-butyl, cyclohexyl, phenyl, and benzyl.

5. The compound according to claim 1, wherein $W^1$ is chosen from the substituent of Formula (I-b), wherein $R^4$ is methyl.

6. The compound according to claim 1, wherein each $W^2$ and $W^3$ is independently chosen from hydrogen and the substituent of Formula (I-a) and Formula (I-b), wherein $R^1$, $R^2$, $R^3$, and $R^4$ are independently chosen from hydrogen, methyl, ethyl, n-propyl, isopropyl, tert-butyl, cyclohexyl, phenyl, and benzyl; and $Y^1$ is chosen from a bond and —O—.

7. The compound according to claim 1, wherein each $W^2$ and $W^3$ is independently chosen from hydrogen and the substituent of Formula (I-a), wherein $R^1$ is chosen from methyl, ethyl, isopropyl, tert-butyl, cyclohexyl, phenyl, and benzyl; $R^2$ and $R^3$ are hydrogen; and $Y^1$ is a bond.

8. The compound according to claim 1, wherein each $W^2$ and $W^3$ is independently chosen from hydrogen and the substituent of Formula (I-b), wherein $R^4$ is chosen from methyl, ethyl, isopropyl, tert-butyl, cyclohexyl, phenyl, and benzyl.

9. The compound according to claim 1, wherein each $W^2$ and $W^3$ is independently chosen from hydrogen and the substituent of Formula (I-b), wherein $R^4$ is methyl.

10. The compound according to claim 1, wherein $W^1$ is chosen from the substituent of Formula (I-a) and Formula (I-b); and each $W^2$ and $W^3$ is independently chosen from hydrogen and the substituents of Formula (I-a) and Formula (I-b); wherein $R^1$, $R^2$, $R^3$, and $R^4$ are independently chosen from hydrogen, methyl, ethyl, n-propyl, isopropyl, tert-butyl, cyclohexyl, phenyl, and benzyl; and $Y^1$ is chosen from a bond and —O—.

11. The compound according to claim 1, wherein $W^1$ and $W^3$ are the substituent of Formula (I-a); and each $W^2$ is hydrogen; wherein $R^1$ is methyl, $R^2$ and $R^3$ are hydrogen, and $Y^1$ is a bond.

12. The compound according to claim 1, wherein $W^1$ and $W^3$ are the substituent of Formula (I-a); and each $W^2$ is hydrogen; wherein $R^1$ is isopropyl, $R^2$ and $R^3$ are hydrogen, and $Y^1$ is a bond.

13. The compound according to claim 1, wherein $W^1$ and $W^3$ are the substituent of Formula (I-b); and each $W^2$ is hydrogen; wherein $R^4$ is methyl.

14. The compound according to claim 1, wherein the compound is chosen from the compounds of Formula (I-A-1), Formula (I-A-4), Formula (I-A-5), Formula (I-A-6), Formula (I-A-7), and Formula (I-F-1), or a pharmaceutically acceptable salt of any of the foregoing:

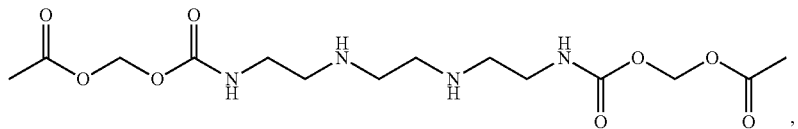

(I-A-1)

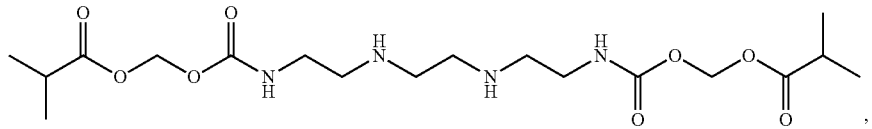

(I-A-4)

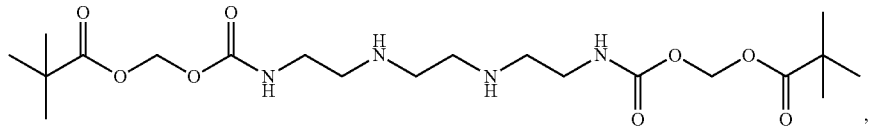

(I-A-5)

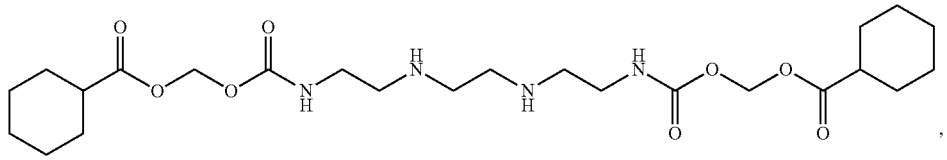

(I-A-6)

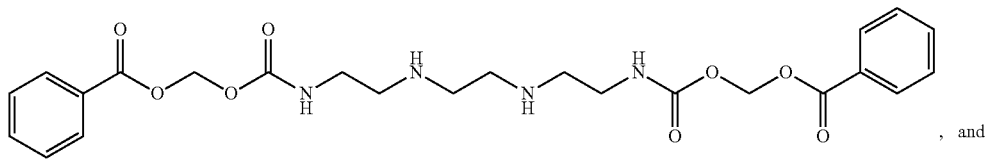

(I-A-7)

, and

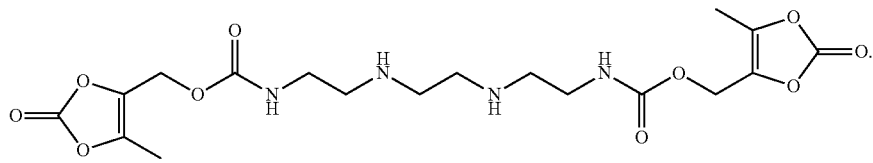

(I-F-1)

15. A pharmaceutical composition comprising a pharmaceutically acceptable vehicle and a therapeutically effective amount of a compound selected from the compounds listed in claim 14.

16. The pharmaceutical composition according to claim 15, wherein the composition is suitable for oral administration.

17. The pharmaceutical composition according to claim 15, wherein the compound is present in an amount that is effective for the treatment of a disease chosen from a liver disease, a kidney disease, and a neurodegenerative disease.

18. The pharmaceutical composition according to claim 15, wherein the compound is present in an amount that is effective for the treatment of Wilson's disease.

19. The pharmaceutical composition according to claim 15, wherein the composition is suitable for controlled release formulation.

20. The pharmaceutical composition according to claim 15, wherein the composition is suitable for sustained release formulation.

* * * * *